(12) United States Patent
Taton et al.

(10) Patent No.: US 8,815,259 B2
(45) Date of Patent: Aug. 26, 2014

(54) DRUG ELUTING SUPERHYDROPHOBIC COATINGS

(75) Inventors: Kristin S. Taton, Little Canada, MN (US); Patrick E. Guire, Hopkins, MN (US); Laurie R. Lawin, New Brighton, MN (US); Jie Wen, Eden Prairie, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 476 days.

(21) Appl. No.: 13/119,756

(22) PCT Filed: Sep. 15, 2009

(86) PCT No.: PCT/US2009/056920
§ 371 (c)(1),
(2), (4) Date: May 23, 2011

(87) PCT Pub. No.: WO2010/033482
PCT Pub. Date: Mar. 25, 2010

(65) Prior Publication Data
US 2011/0223212 A1    Sep. 15, 2011

Related U.S. Application Data

(60) Provisional application No. 61/098,324, filed on Sep. 19, 2008.

(51) Int. Cl.
*A61K 9/00* (2006.01)
*A61F 2/00* (2006.01)
*A61K 31/17* (2006.01)

(52) U.S. Cl.
USPC ............................ 424/400; 424/425; 514/588

(58) Field of Classification Search
USPC .................................. 424/400, 425; 514/488
See application file for complete search history.

(56) References Cited

U.S. PATENT DOCUMENTS

| | | | |
|---|---|---|---|
| 3,580,927 A | 5/1971 | Wear | |
| 4,731,080 A | 3/1988 | Galin | |
| 6,096,070 A | 8/2000 | Ragheb et al. | |
| 2003/0147932 A1 | 8/2003 | Nun et al. | |
| 2004/0162609 A1 | 8/2004 | Hossainy et al. | |
| 2005/0181015 A1 | 8/2005 | Zhong | |
| 2006/0204738 A1 | 9/2006 | Dubrow | |
| 2009/0186070 A1* | 7/2009 | Guire et al. ................ | 424/426 |

FOREIGN PATENT DOCUMENTS

| | | |
|---|---|---|
| EP | 1283077 A1 | 1/2003 |
| JP | 57-042742 | 3/1982 |
| JP | 57-117564 | 7/1982 |
| JP | 59-043061 | 3/1984 |
| WO | WO 98/03489 | 1/1998 |
| WO | WO 01/40367 | 6/2001 |
| WO | WO 03/030879 A1 | 4/2003 |
| WO | WO 2005/107455 A2 | 11/2005 |
| WO | WO 2007/092179 | 8/2007 |
| WO | WO 2008/106494 A1 | 9/2008 |

OTHER PUBLICATIONS

Extended European Search Report from related PCT Application PCT/US2009/056920, dated May 9, 2013, 6 pages.
International Search Report and Written Opinion from related PCT Application PCT/US2009/056920, dated Oct. 29, 2009, 12 pages.
International Preliminary Report on Patentability from related PCT Application PCT/US2009/056920, dated Mar. 22, 2011, 8 pages.

* cited by examiner

*Primary Examiner* — Abigail Fisher
(74) *Attorney, Agent, or Firm* — Fulbright & Jaworski LLP; Scott D. Rothenberger

(57) ABSTRACT

The invention describes nanotextured super hydrophobic coatings that contain active agents which can elute from the coating over a period of time.

11 Claims, 2 Drawing Sheets

DRUG ELUTING SUPERHYDROPHOBIC COATINGS

CROSS REFERENCE TO RELATED APPLICATIONS

This application is a Section 371 National Stage Application of International No. PCT/US2009/056920, filed Sep. 15, 2009 and published as WO 2010/033482 A1 on Mar. 25, 2010, which claims priority from U.S. Provisional Application 61/098,324, filed Sep. 19, 2008, the contents of which are incorporated herein in their entirety for all purposes.

FIELD OF THE INVENTION

The invention relates generally to superhydrophobic coatings that contain bioactive agents, such as antimicrobials, anti-inflammatories, or antibiotics, that surprisingly, release the bioactive agent over a period of time under aqueous conditions, e.g., physiological conditions.

BACKGROUND OF THE INVENTION

Many applications involve the interaction of liquids with solid surfaces. Often, it is desirable to control or influence the manner of the interaction, particularly the degree of wetting of the surface, so as to achieve a specific result. As an example, surfactants are sometimes added to liquids used in cleaning processes to achieve increased surface wetting. Conversely, liquid repellent coatings are sometimes added to products to reduce surface wetting and accelerate drying of the surface.

The principles and properties affecting surface wetting have been studied for decades to understand physical/chemical interactions that effect the nature of the surface. There has been and continues to be a particular interest in surfaces that are resistant to wetting by liquids. Such surfaces are referred to as hydrophobic where the liquid is water, and lyophobic relative to other liquids.

Interestingly, medical devices such as catheters, ventilation tubes, endotracheal and the like generally are treated with hydrophilic or lubricious coating, helping to reduce friction between the body lumen and the device upon insertion. However, such coatings once in contact with body fluids become a fertile breeding ground for bacteria. Infections can result from prolonged usage of such devices in the body.

For example, invasive medical devices are strongly associated with 68% of the country's 2 million plus nosocomial infections. These infections cost billions of dollars, wasted resources, and of course sadly, many lives. The introduction of new coatings which combat bacterial colonization would be a significant milestone in reducing nosocomial infections.

Therefore, a need exists for coatings and medical devices having coatings that can be inserted into a body lumen without discomfort and with the ability to remain in the lumen for extended periods of time without becoming a site for infection.

BRIEF SUMMARY OF THE INVENTION

The present invention surprisingly provides coatings which can be applied to a surface, such as a medical device, that provide super hydrophobic characteristics while also providing a drug that can elute from the coating over a period of time. With the release of the drug from the coating, reduction of or elimination of bacteria is accomplished, thereby providing the option of leaving the device in a body lumen for extended periods of time without becoming a site of infection.

The present invention also provides method to treat or coat substrates, such as medical devices, with the coating compositions of the invention.

In one aspect, the present invention provides a coating that includes a first hydrophobic binder, a plurality of particles comprising a size between about 1 nm to about 25 microns and a bioactive agent. In one embodiment, the particles are dispersed throughout the bulk of the coating. In another embodiment, the coating can be applied to a medical device, such as an endotracheal tube.

In another aspect, the present invention provides a bilayer composition that includes a first layer having a bioactive agent and a second layer having a hydrophobic binder and a plurality of particles comprising a size between about 1 nm to about 25 microns. In one embodiment, the particles are dispersed throughout the bulk of the second layer.

The coatings of the invention help control of infection from non-sterile surfaces by reduction of colonization on the surfaces. Not to be limited by theory, it is believed that this is accomplished, at least in part by, prevention of adhesion on and/or transfer to the surface from contaminated surfaces, and/or prevention of growth of microorganisms on the coated surface. This may be accomplished by prevention of wetting of the coated surface by non-sterile aqueous liquids (or other methods of reducing adhesion), and/or prevention of growth by release, upon becoming wet, of antimicrobial agents (which prevent/inhibit microbial proliferation by direct interaction with microbes or promote other antimicrobial functions, such as phagocytosis, etc.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
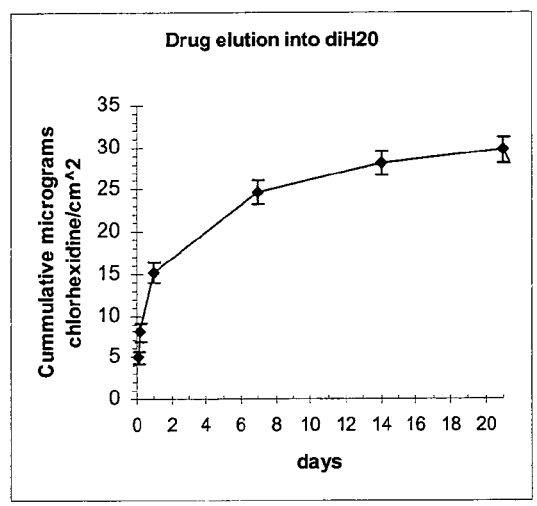
FIG. 1 depicts a chlorhexidine release curve for 21 days of elution from a coating of the invention.

In the specification and in the claims, the terms "including" and "comprising" are open-ended terms and should be interpreted to mean "including, but not limited to...." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The invention surprisingly provides super hydrophobic drug delivery coatings for medical devices. The present invention takes a two-pronged approach to antimicrobial coating—superhydrophobicity and drug delivery. Superhydrophobic surfaces repel water readily and do not only minimize bacterial transfer during insertion, but also inhibit bacterial adhesion initially. Unfortunately, once in the body, superhydrophobic surfaces eventually lose this property, and will come into full contact with body fluids. At that point, drug release from the same coating inhibits bacterial colonization and biofilm formation. Typically drug delivery coatings release with an initial burst of drug, followed by longer release of lesser amounts. For nosocomial infections, which can develop long after the initial insertion, the burst is also delayed or the drug release amounts or/and rates are modulated. However, by using a super hydrophobic surface to delay contact with the body fluids, the burst is also delayed. By combining these two approaches to antimicrobial surfaces, the effectiveness of the coating has now been enhanced. This is the first suggested use of superhydrophobicity on a medical device with or without drug release. Prior to the present invention, it would have seemed counterintuitive to consider using a super hydrophobic coating to deliver a drug. It would have seemed that due to the hydrophobicity of the coating, the drug would have not eluted. Additionally, the super hydrophobic polymer matrix appears to provide protection to the bioactive agent from the effects of radiation, for example, ultra-violet radiation as well as to be a flexible and conformal on the substrate of a device surface.

In one particular application, the present invention addresses the need for coating endotracheal tubes to reduce ventilator-associated pneumonia (VAP) in mechanically ventilated patients. However, the coatings presented herein are broadly applicable to not only other medical devices, but also other hospital equipment, and various water- and food-contacting surfaces.

Ventilator-associated pneumonia is a complex disease defined as occurring after 48 hours of intubation. Early-onset VAP (4-7 days intubation) is believed to be initiated by the introduction of the endotracheal tube through the mouth and into the trachea. Despite suction, the somewhat tortous passage of the tube may lead to bacteria from the mouth and nasal passages lower into the respiratory tract where they can then be microaspirated into the lungs. Other complications include injury to the trachea, pooling of secretions near the cuff of the endotracheal tube, and aspiration from the stomach/gastric region. Commonly *Staphylococcus aureus, Streptococcus pneumoniae*, and *Haemophilus influenzae* are associated with early onset VAP, while methicillin-resistant *Staph aureus, Pseudomonas aeruginosa*, and *Aceintobacter baumannii* are encountered in late onset VAP with most cases involving multiple bacteria. Over time these bacteria form a biofilm covering the endotracheal tube. Late onset VAP bacteria are truly nosocomial, while early onset are frequently present prior to hospitalization. Current strategies for preventing VAP include semi-recumbent positioning, frequent suctioning, limited changes to the ventilator circuit, and selective digestive tract decontamination and prophylactic antibiotic treatment (these last two may increase antibiotic resistance). While these do have the potential to lower VAP rates, new strategies are necessary.

For endotracheal tubes, superhydrophobic coatings has two advantages. First, initial insertion of the tube transfers much less bacteria into the lower respiratory tract because saliva does not adsorb to the tube. Second, bacterial biofilm formation is lessened due to lack of adhesion. Averting biofilm formation on the endotracheal tube eliminates a major source of late bacterial colonization, and minimizes late onset VAP as well. Other sources of bacteria are present in many mechanically ventilated patients, including even their own stomachs, as well as the ventilation equipment but the tube currently supplies the main route of transmission to the lungs.

While super hydrophobic endotracheal tubes significantly diminish bacterial colonization, chlorhexidine was also included into the coatings to provide a second line of defense. In the absence of bacteria or other adherence on the tube, the chlorhexidine would remain in the coating. Over time in the body, the superhydrophobicity of the coating is eventually be lost. This is due to a number of factors, primarily the pressure of the trachea on the coating and the presence of proteins and other biomolecules which act as surfactants lowering the surface tension of the water and promoting contact between the surface and the bodily fluids. When saliva contacts the tube, the chlorhexidine, or other bioactive agent, diffuses out of the coating for bactericidal action. This dual-pronged approach applies to both late and early onset VAP, as well as being applicable to other medical devices.

One example of a bioactive agent, is chlorhexidine. Chlorhexidine is a bisdiguanide antiseptic commonly used in the dental and pharmaceutical industries. It is active against a broad spectrum of both Gram positive and Gram negative bacteria and particularly useful as an anti-plaque agent for the mouth. It is currently used commercially on central venous catheters with good effect.

With the above outline, the broad scope and applications of the invention will now be discussed.

The coatings of the invention can be applied to a large variety of substrates including but not limited to plastics (polyethylene, polypropylene, nylon, silicone rubber, PVC, polystyrene, polyurethane, etc.), glass, natural polymers, such as wood (cellulose), polysaccharides, proteins, paper, ceramics, metals and composites. The hydrophobic binder is optimally hydrophobic (surface tension <50 mN/m) and can contain reactive groups such as double bonds, but is not required to. The nanoparticles should also be hydrophobic. The polymeric binder matrix entraps the nanoparticles to provide nanotexture that imparts super hydrophobicity.

In one aspect, the present invention provides a coating that includes a first hydrophobic binder, a plurality of particles comprising a size between about 1 nm to about 25 microns and a bioactive agent. In one embodiment, the particles are dispersed throughout the bulk of the coating. In another embodiment, the coating can be applied to a medical device, such as an endotracheal tube. In yet another embodiment, the bioactive agent is encapsulated within a second binder prior to incorporation into the first hydrophobic binder, wherein the first and second binders can be the same or different, provided the first binder is hydrophobic.

The coatings described herein are super hydrophobic. A surface is defined as being superhydrophobic if a stream of water is repelled by the surface as shown by water droplets bouncing off of the surface and/or if a ten microliter water droplet applied manually by a micropipette cannot be placed on the level surface without rolling.

Generally the thickness of the coatings of the invention are between about 0.02 microns and about 1000 microns, in particular between about 0.2 microns and about 100 microns and most particularly between about 0.5 microns and about 20 microns.

The hydrophobic first binder can be selected from those materials listed herein that provide hydrophobic characteristics.

It should be understood that the term "polymeric binder" is a polymer that is not a prepolymer in that polymeric resins utilized in the present invention include only random reactive sites or a minimal degree of unsaturation found within the polymeric chain. A prepolymer as used herein, is a reactive low-molecular weight macromolecule or oligomer capable of further polymerization.

Generally, the polymeric binder has less than about 1% mol %, less than about 0.5% mol %, less than about 0.05% mol % and in particular less than about 0.02% mol % alkylenic reactive sites of unsaturation, e.g., vinyl double bonds.

The polymeric binders useful in the invention are film forming which is meant to include polymers and low molecular mass substances which form a solid film on a surface. The binders serve, for example, to fix the particles on the surface of the substrate to be coated or to fix the particle surfaces to one another.

The hydrophobicity of the binder is characterized by its surface tension. This may be determined, for example, by measuring the static contact angle of water on a smooth surface coated with the binder. It may also be determined by the pendant drop method. Hydrophobic binders useful in the present invention have a surface tension <50 mN/m. The surface tension of commercially customary binder polymers are in some cases indicated in the literature; see, e.g. Wu et al., op. cit. p. 88 ff. and also S. Ellefson et al., J. Am. Ceram. Soc. 21, 193, (1938); S. Wu, J. Colloid Interface Sci. 31, (1969), 153, J. Phys. Chem. 74, (1970), 632, J. Polym. Sci. C34 (1971) 19; R. J. Roe et al., J. Phys. Chem. 72, 2013 (1968), J. Phys. Chem. 71 (1967) 4190, J. Colloid Interface Sci. 31, (1969) 228; and J. F. Padday in Surface and Colloid Science (edited by E. Matijevic), Wiley, N.Y. 1969, pp. 101-149, the contents of which are incorporated herein in the entirety for all purposes.

In particular, binders which have a surface energy <45 mN/m, more particularly, <40, even more particularly, <35 and in particular <30 mN/m are of interest for use with the present invention.

The binders generally comprise thermoplastic polymers which are soluble in organic solvents. The binders used may also comprise organic prepolymers which are polymerized or crosslinked by a thermal, oxidative or photochemical curing process and so form a solid coating with the powder.

Polymeric binders include, for example fatty acids having more than 8 carbon atoms, natural waxes such as beeswax, carnauba wax, wool wax, candelilla wax, and also synthetic waxes such as montanic acid waxes, montanic ester waxes, amide waxes, e.g., distearoylethylenediamine, Fischer-Tropsch waxes, and also waxlike polymers of ethylene and of propylene (polyethylene wax, polypropylene wax).

The nature of the binder is of fairly minor importance for the success of the invention, provided the binder is sufficiently hydrophobic.

For example, hydrophobic monomers useful to prepare polyalkylene polymeric binders include C2-C24 olefins, C5-C8 cycloolefins, fluoroolefins, fluorochloroolefins, vinyl aromatics, diolefins such as butadiene, isoprene and chlorobutadiene, and different monoethylenically unsaturated monomers that can contain at least one C2-C36 alkyl group.

Suitable examples of hydrophobic monomers useful to prepare polyalkylene polymeric binders include C2-C24 olefins, such as ethylene, propylene, n-butene, isobutene, n-hexene, n-octene, isooctene, n-decene, isotridecene.

Suitable examples of hydrophobic monomers useful to prepare polycylcloalkylene polymeric binders include C5-C8 cycloolefins such as cyclopentene, cyclopentadiene, cyclooctene.

Suitable examples of hydrophobic monomers useful to prepare polyvinylarylenes polymeric binders include vinyl aromatic monomers such as styrene and alpha-methylstyrene.

Suitable examples of hydrophobic monomers useful to prepare fluorinated polyalkylene polymeric binders include fluoroolefins and fluorochloroolefins such as vinylidene fluoride, chlorotrifluoroethylene and tetrafluoroethylene.

Suitable examples of hydrophobic monomers useful to prepare polyvinyl esters polymeric binders include vinyl esters of linear or branched alkane carboxylic acids having 2 to 36 carbon atoms such as vinyl acetate, vinyl propionate, vinyl n-butyrate, vinyl isobutyrate, vinyl hexanoate, vinyl octanoate, vinyl laurate and vinyl stearate.

Suitable examples of hydrophobic monomers useful to prepare polyacrylate and polymethacrylate polymeric binders include esters of acrylic acid and of methacrylic acid with linear or branched C1-C36 alkanols, e.g., ethyl (meth)acrylate, n-butyl (meth)acrylate, tert-butyl (meth)acrylate, n-hexyl (meth)acrylate, 2-ethylhexyl (meth)acrylate, 2-propylheptyl (meth)acrylate, lauryl (meth)acrylate and stearyl (meth)acrylate and also vinyl ethers (polyvinyl ethers) and allyl ethers (polyallylethers) of C2-C36 alkanols, such as n-butyl vinyl ether and octadecyl vinyl ether.

Still other suitable examples of hydrophobic polymeric binders useful in the invention include poly-C3-C6-alkylene oxides, such as polypropylene oxide and polybutylene oxide, polytetrahydrofuran and also polycaprolactone, polycarbonates, polyvinylbutyral, polyvinylformal, and also linear or branched polydialkylsiloxanes such as polydimethylsiloxane (silicones).

Yet still other suitable examples of hydrophobic polymeric binders include polyesters made from aliphatic or aromatic dicarboxylic acids and aliphatic and/or aromatic diols, e.g.: polyesters synthesized from aliphatic dialcohols having 2 to 18 carbon atoms, e.g., propanediol, butanediol, hexanediol, and dicarboxylic acids having 3 to 18 carbon atoms, such as adipic acid and decanedicarboxylic acid; polyesters synthesized from bisphenol A and the abovementioned dicarboxylic acids having 3 to 18 carbon atoms; and polyesters synthesized from terephthalic acid, aliphatic dialcohols having 2 to 18 carbon atoms, and dicarboxylic acids having from 3 to 18 carbon atoms.

The polyesters may optionally be terminated by long-chain monoalcohols having 4 to 24 carbon atoms, such as 2-ethyl hexanol or octadecanol. Furthermore, the polyesters may be terminated by long-chain monocarboxylic acids having 4 to 24 carbon atoms, such as stearic acid.

Other suitable examples of hydrophobic polymeric binders include polyamides made from aliphatic or aromatic dicarboxylic esters or acid halides and aliphatic and/or aromatic amines, e.g.: polyesters synthesized from aliphatic diamines having 2 to 18 carbon atoms, e.g., propanediamine, butanediamine, hexanediamine, and dicarboxylic esters or acid halides having 3 to 18 carbon atoms, such as adipic acid esters and decanedicarboxylic acid diesters; polyamides synthesized from bisphenylamine A and the abovementioned dicarboxylic esters having 3 to 18 carbon atoms; and polyesters synthesized from terephthalic esters, aliphatic diaamines having 2 to 18 carbon atoms, and dicarboxylic esters having from 3 to 18 carbon atoms.

The polyamides may optionally be terminated by long-chain monoalcohols or monoamines having 4 to 24 carbon atoms, such as 2-ethyl hexanol or octadecanol. Furthermore, the polyamides may be terminated by long-chain monocarboxylic acids having 4 to 24 carbon atoms, such as stearic acid.

As used herein, the term "polyurethane/polyurea" refers to a polymer containing urethane linkages, urea linkages or combinations thereof. Typically, such polymers are formed by combining diisocyanates with alcohols and/or amines. For example, combining isophorone diisocyanate with a diol and a diamine under polymerizing conditions provides a polyurethane/polyurea composition having both urethane (carbamate) linkages and urea linkages. Such materials are typically prepared from the reaction of a diisocyanate and a polymer having a reactive portion (diol, diamine or hydroxyl and amine), and optionally, a chain extender.

Suitable diisocyanates include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate), isophorone diisocyanate (IPDI) and 4,4'-methylenebis(cyclohexyl isocyanate). A number of these diisocyanates are available from commercial sources such as Aldrich Chemical Company Milwaukee, Wis., USA) or can be readily prepared by standard synthetic methods using literature procedures.

The alcoholic or amine containing polymer can be a diol, a diamine or a combination thereof. The diol can be a poly(alkylene)diol, a polyester-based diol, or a polycarbonate diol. As used herein, the term "poly(alkylene)diol" refers to polymers of alkylene glycols such as poly(ethylene)diol, poly(propylene)diol and polytetramethylene ether diol. The term "polyester-based diol" refers to a polymer in which the R group is a lower alkylene group such as ethylene, 1,3-propylene, 1,2-propylene, 1,4-butylene, 2,2-dimethyl-1,3-propylene, and the like. One of skill in the art will also understand that the diester portion of the polymer can also vary. For example, the present invention also contemplates the use of succinic acid esters, glutaric acid esters and the like. The term "polycarbonate diol" refers those polymers having hydroxyl functionality at the chain termini and ether and carbonate functionality within the polymer chain. The alkyl portion of the polymer will typically be composed of C2 to C4 aliphatic radicals, or in some embodiments, longer chain aliphatic radicals, cycloaliphatic radicals or aromatic radicals. The term diamines refers to any of the above diols in which the terminal hydroxyl groups have been replaced by reactive amine groups or in which the terminal hydroxyl groups have been derivatized to produce an extended chain having terminal amine groups. These polymers can be obtained from Aldrich Chemical Company. Alternatively, literature methods can be employed for their synthesis.

The amount of alcoholic or amino polymer which is used in the present compositions will typically be about 10% to about 100% by mole relative to the diisocyanate which is used. Preferably, the amount is from about 50% to about 90% by mole relative to the diisocyanate. When amounts less than 100% of polymer are used, the remaining percentage (up to 100%) will be a chain extender.

In certain embodiments, the polymeric polyurethane binders will also contain a chain extender which is an aliphatic or aromatic diol, an aliphatic or aromatic diamine, alkanolamine, or combinations thereof. Examples of suitable aliphatic chain extenders include ethylene glycol, propylene glycol, 1,4-butanediol, 1,6-hexanediol, ethanolamine, ethylene diamine, butane diamine, 1,6-hexamethylenediamine, 1,2-diaminocyclohexane or isophorone diamine and 1,4-cyclohexanedimethanol. Aromatic chain extenders include, for example, para-di(2-hydroxyethoxy)benzene, meta-di(2-hydroxyethoxy)benzene, (2,4-diamino-3,5-di(methylthio)toluene), 3,3'-dichloro-4,4' diaminodiphenylmethane, trimethylene glycol bis(para-aminobenzoate)ester and methylenedianiline. In one aspect, the chain extender is present an amount of from about 10% to 50% by mole relative to the diisocyanate.

Cellulosic binders are also useful polymers in this invention. Suitable cellulose polymers include, methyl cellulose, ethyl cellulose, hydroxymethyl cellulose, hydroxyethyl cellulose, hydroxypropyl cellulose, cellulose acetate, and cyanoethylated cellulose.

Other suitable polymeric binders include, for example, homo and copolymers of polyacrylonitriles, polymethacrylonitriles, poly(alkyl)acrylates, polyesters, polyurethanes, polycyanoacrylates, polycyanomethacrylates, poly(ethylene-propylene), polybutadienes, poly(cis-1,4-isoprenes), poly(trans-1,4-isoprenes), polychloroprenes (neoprene), poly(vinyl chlorides), poly(vinyl fluorides), poly(vinylidine chlorides), poly(vinylidine fluorides), poly(chlorotrifluoroethylene-vinylidine fluoride), poly(tetrafluoro-ethylene-hexafluoropropylene), poly(vinyl acetates), poly(methylvinylethers), poly(isobutyl vinyl ethers), poly(vinyl)laurates, poly(vinyl)stearates, poly(vinyl)neodecanoates, poly(vinyl-neononanoates), polyvinyl alcohols, poly(vinylbutyrals), poly(methyl vinyl ketones), poly(vinylpyrrolidones), poly(N-vinylcarbazoles), poly(acrylonitrile-butadienes), poly(acrylonitrile-butadiene-styrenes), poly(acrylonitrile-vinyl chlorides), poly(styrene-butadienes), polystyrenes, poly(styrene-alpha-methylstyrenes), polyethylene-vinylacetate polymers, poly(vinylidine fluoride-hexafluoropropylene), poly(vinyl chloride-vinyl acetates), poly(phenolformaldehyde) resins, poly(imino(1-oxoundecamethylenes), poly(iminoadipoyl iminohexamethylenes), poly(hexamethylene adipamide)s, poly(hexamethylene sebacamide)s, poly(hexamethylene dodecanediamides), poly(iminoadipoyliminotetramethylenes), poly(butyleneadipides), poly(iminoadipoyliminopentamethylenes), poly(pentaleneadipides) poly(amides), poly(imino(1-oxotetramethylenes), (polypyrrolidinones), poly[imino(1-oxo-2,2-dimethyl-3-phenyltrimethylene)]poly(amides), poly(lysine-co-lactic acid) (1:19) poly(amides), poly(aspartic acid-co-lactic acid) (1:9) poly(amides). poly(ethylene terephthalates), poly(butylene terephthalates), poly(4,4'-carbonato-2,2-diphenylpropanes), poly(lactic-co-glycolic acid)/poly-L-lactide (PLGA/PLLA), poly(ethylene oxides), poly(ethyleneglycol methacrylates), polytetrahydrofurans, poly(tetramethylene ether glycols), poly(epichlorohydrins), poly(epichlorohydrin-ethylene oxides), poly(butylene glycols), polyformaldehydes, poly(phenylene sulfides), poly(trimethylene sulfides), poly(ether ether ketones), poly(iminocarbonyl-phenylethylidenes), poly-L-phenylalanines, polyphosphazenes, poly[bis(trifluoroethoxy)-polyphosphazenes, poly[bis(trifluoroethoxy)-phosphazenes], poly(dimethylsiloxane-co-diphenylsiloxanes), poly (dimethylsiloxanes) (silicone rubber), poly(melamine-formaldehydes), poly(urea-formaldehyde) resins and Udel polysulfone, poly(oxy-1,4-cyclohexyleneoxycarbonylimino-1,4-phenylenemethylene-1,4-phenyleneiminocarbonyls), polycarbonates, polyanhydrides and polyorthoesters.

The weight-average molecular weight of the polymeric binders may vary over a wide range and is generally in the range from 1000 to 30 million g/mol and preferably in the range from 2500 to 6 million, in particular 2500 to 5 million.

The weight ratio of particle to binder is one consideration for creating hydrophobic coatings of the invention. Depending on the density of the particles used, the ratio will vary and a person of skill in the art will adjust the ratio (weight) of the particle to binder (weight) according to the ultimate property desired. In general, coatings made of low density particles will have lower particle concentration requirements. Conversely, coatings made with higher density particles will have higher particle concentration requirements. For example, silica particle materials have varying densities, depending on porosity and the nature of the silica. In certain embodiments, the ratio of typical (e.g., silica) particles to polymeric binder is about 1:1 to about 4:1, between about 1.1:1 to about 3:1, and more particularly between about 1.2:1 and about 2:1.

The particles include those particles having a particle size of between about 1 nm and about 25 micron sized particles that can be porous or non-porous particles derived from aluminum oxides (alumina), titanium oxide, zirconium oxide, gold (treated with organo thiols), silver (organo thiol or silane treated), nickel, nickel oxide, iron oxide, and alloys (all treated with silane), polystyrene particles, (meth)acrylates particles, PTFE particles, silica particles, polyolefin particles, polycarbonate particles, polysiloxane particles, silicone particles, polyhedral oligomeric silsesquioxanes, polyhedral oligomeric silicates, polyester particles, polyamide particles, polyurethane particles, ethylenically unsaturated polymer particles, polyanhydride particles and biodegradable particles such as polycaprolactone (PCL) and polylactideglycolide (PLGA), and nanofibers, nanotubes, or nanowires and combinations thereof. Appropriate treatments of the metals, such as gold, silver, and other nobel metals and alloys are generally include use of alkylthiols, more particularly fluoroalkylthiols.

Generally inorganic particles, porous or non-porous, are pretreated with a silane to promote hydrophobicity.

As briefly described above, the polymer matrix includes a bioactive agent for sustained delivery of the bioactive agent to a treatment site. As used herein, "bioactive agent" refers to an agent that affects physiology of biological tissue. Bioactive agents useful according to the invention include virtually any substance that possesses desirable therapeutic and/or prophylactic characteristics for application to the implantation site.

For ease of discussion, reference will repeatedly be made to a "bioactive agent." While reference will be made to a "bioactive agent," it will be understood that the invention can provide any number of bioactive agents to a treatment site. Thus, reference to the singular form of "bioactive agent" is intended to encompass the plural form as well.

Exemplary bioactive agents include, but are not limited to, thrombin inhibitors; antithrombogenic agents; thrombolytic agents (such as plasminogen activator, or TPA: and streptokinase); fibrinolytic agents; vasospasm inhibitors; calcium channel blockers; vasodilators; antihypertensive agents; clotting cascade factors (for example, protein S); anti-coagulant compounds (for example, heparin and nadroparin, or low molecular weight heparin); antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephapirin, cefazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone), geldanamycin and analogues, antifungals (such as amphotericin B and miconazole), and antivirals (such as idoxuridine trifluorothymidine, acyclovir, gancyclovir, interferon, .alpha.-methyl-P-adamantane methylamine, hydroxy-ethoxymethyl-guanine, adamantanamine, 5-iodo-deoxyuridine, trifluorothymidine, interferon, adenine arabinoside); inhibitors of surface glycoprotein receptors; antiplatelet agents (for example, ticlopidine); antimitotics; microtubule inhibitors; anti-secretory agents; active inhibitors; remodeling inhibitors; antisense nucleotides (such as morpholino phosphorodiamidate oligomer); anti-metabolites; antiproliferatives (including antiangiogenesis agents, taxol, sirolimus (rapamycin), analogues of rapamycin ("rapalogs"), tacrolimus, ABT-578 from Abbott, everolimus, paclitaxel, taxane, vinorelbine); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); mydriatics (such as atropine, cyclopentolate, homatropine, scopolamine, tropicamide, eucatropine, hydroxyamphetamine); sympathomimetics (such as epinephrine); antineoplastics (such as carmustine, cisplatin, fluorouracil); immunological drugs (such as vaccines and immune stimulants); hormonal agents (such as estrogens, estradiol, progesterol, progesterone, insulin, calcitonin, parathyroid hormone, peptide and vasopressin hypothalamus releasing factor); beta adrenergic blockers (such as timolol maleate, levobunolol HCl, betaxolol HCl); immunosuppressive agents, growth hormone antagonists, growth factors (such as epidermal growth factor, fibroblast growth factor, platelet derived growth factor, transforming growth factor beta, somatotropin, fibronectin, insulin-like growth factor (IGF)); carbonic anhydrase inhibitors (such as dichlorophenamide, acetazolamide, methazolamide); inhibitors of angiogenesis (such as angiostatin, anecortave acetate, thrombospondin, anti-VEGF antibody such as anti-VEGF fragment—ranibizumab (Lucentis)); dopamine agonists; radiotherapeutic agents; peptides; proteins; enzymes; nucleic acids and nucleic acid fragments; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Another group of useful bioactive agents are antiseptics. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Another group of useful bioactive agents are enzyme inhibitors. Examples of enzyme inhibitors include chrophonium chloride, N-methylphysostigmine, neostigmine bromide, physostigmine sulfate, tacrine HCL, tacrine, 1-hydroxymaleate, iodotubercidin, p-bromotetraminsole, 10-(.alpha.-diethylaminopropionyl)-phenothiazine hydrochloride, calmidazolium chloride, hemicholinium-3,3,5-dinitrocatechol, diacylglycerol kinase inhibitor 1, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−)deprenyl HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-.alpha.-methylbenzylamine (DCMB), 8,9-dichloro-2,3,4,5-tetrahydro-1H-2-benzazepine hydrochloride, p-aminoglutethimide, p-aminoglutethimide tartrate, R(+) p-aminoglutethimide tartrate, S(−)3-iodotyrosine, alpha-methyltyrosine, L(−)alpha methyltyrosine, D,L(−)cetazolamide, dichlorophenamide, 6-hydroxy-2-benzothiazolesulfonamide, and allopurinol.

Another group of useful bioactive agents are anti-pyretics and antiinflammatory agents. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances that have an anesthetic effect in a localized region. Examples of such anesthetics include procaine, lidocaine, tetracaine and dibucaine.

In some embodiments, the bioactive agent delivery system comprises bioactive agent and a polymeric material. That is, the bioactive agent can be encapsulated by a polymeric binder that can be hydrophilic or hydrophobic. Any polymeric material capable of delivering bioactive agents in accordance with the principles of the invention can be utilized. Some illustrative polymeric materials are described herein, without limitation.

Suitable polymeric binder, referred to as second polymeric binders, include hydrophilic and hydrophobic binders, for example, homopolymers and copolymers of polymethacrylates, polyacrylates, polycarbonates, polyolefins, polyurethanes, acrylonitrile, polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyesters, polyisoprene, polyisobutylene, polybutadiene, polyetherketones, polyethylene, polyethers, polytetrafluoroethylene, polychloroethers, polyvinyl acetates, nylons, silicone rubbers and elatomers, polydimethylsiloxanes, polyvinylpyrrolidone, polyvinylalcohols, cellulose, polyanhydrides, polyorthoesters, polycaprolactone, hyaluronic acid, starch, dextran, heparin, chondroitin sulfate, dermatan sulfate, heparan sulfate, keratan sulfate, dextran sulfate, pentosan polysulfate, and chitosan; and protein (and other polyamino acids), examples of which include but are not limited to gelatin, collagen, fibronectin, laminin, albumin, elastin, and active peptide domains thereof and the like.

It should be understood, that when a hydrophilic binder is used, that the amount of hydrophilic material utilized is minimal so as not to impact the overall super hydrophobicity of the ultimate coating. The use of the hydrophilic binder can help to encapsulate those bioactive agents that otherwise may be hydrophilic and not lend themselves well to a hydrophobic binder. Selection of an appropriate second binder that is then compatible with the hydrophobic binder can help to stabilize the coating so that the bioactive agent can then later elute from the ultimate coating.

Plastics such as polyolefins, polystyrenes, poly(methyl) methacrylates, polyacrylonitriles, poly(vinylacetates), poly (vinyl alcohols), chlorine-containing polymers such as poly (vinyl) chloride, polyoxymethylenes, polycarbonates, polyamides, polyimides, polyurethanes, phenolics, amino-epoxy resins, polyesters, silicones, cellulose-based plastics, and rubber-like plastics can all be used as supports, providing surfaces that can be modified as described herein. See generally, "Plastics", pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon, parylene coated surfaces, and silylated surfaces of glass, ceramic, natural polymers, such as wood (cellulose), polysaccharides, proteins, paper, ceramics, metals or composites are suitable for surface modification.

Once the composition is applied to a substrate, the coating can then be subjected to an energy source suitable to initiate reaction of the initiator and/or the crosslinker.

Not to be limited by theory, the coatings of the invention adhere to the surface of the substrate. It is unknown whether the adhesion is from covalent or ionic attachment, or if any physical attachment actually occurs. However, it has been found that treatment of the coatings where inter- or intrapolymeric crosslinking is accomplished (such as thermal, photoactivation (photopolymerization), radical generation, etc.) often provides a durable coating that is not easily removed.

Photoactivation can be defined as a phenomenon whereby individual substances are joined together to create a new larger structure by way of the action of light. When light is absorbed, electrons populate excited states in molecules. These excited states are generally quite short-lived and terminate by one of three pathways. The excited state can emit a photon from either a singlet state (fluorescence) or a triplet state (phosphorescence), lose its energy via vibrations in the form on heat, or react chemically. Because the absorption of a photon highly excites a molecule, there is a much wider variety of reactions possible than standard thermochemical means. Photocrosslinking uses these reactions to join small to molecules to other small molecules, large molecules to small molecules, and large molecules to each other (photocoupling of polymers), as well as large and small molecules to substrates or particles (photobonding to surfaces). During photocrosslinking each increase in molecular weight is initiated by its own photochemical reaction and the coupling of radicals can result in the formation of crosslinks, especially in the solid state. Photocrosslinking can usually be classified into two types.

The first type is where crosslinks are formed by the direct reaction of an excited molecule. Representative reactions would be a photo 2+2 cycloaddition (or 4+4) and cis-trans isomerization of double bonds. Examples of this type are demonstrated by the cyclodimerization of cinnamic acid and derivatives, chalcones and stilbenes, anthracenes, maleimides and strained cycloalkenes. In another large class of reactions, the triplet, $T_1$ excited state of carbonyl groups in ketones can result in either fragmentation (Norrish Type I reaction) or hydrogen abstraction (Norrish type II reaction). Both of these photoreactions create two radicals which can then subsequently react with surrounding molecules. For example, aromatic ketones, such as benzophenone, readily undergo hydrogen abstraction reactions with any preformed polymer possessing C—H bonds. A possible mechanism is shown in the Scheme which follows.

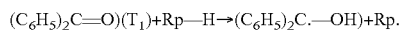

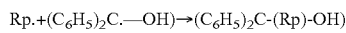

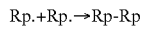

The second usual type of photocrosslinking is where crosslinks occur through the action of a photogenerated reactive species. Examples of the second type include the use of nitrenes that are formed from organic azides and carbenes.

Whether through direct excited state reaction or reactive intermediates, photolysis of photoreactive groups can begin a process of bond formation throughout a mixture. The act of cross linking will serve to increase the durability of this surface. Bonds will be formed between initiators and crosslinkers, crosslinkers and crosslinkers, initiators and initiators, and between crosslinkers and/or initiators and the surface of the substrate. Bond formation may take place by many means within the various systems. In many cases radicals are formed through photolysis. Radicals can form new bonds through radical-radical recombination, addition to unsaturated bonds, hydrogen abstraction and subsequent recombination or addition, further fragmentation, oxygen addition, or disproportionation, as well as possible electron transfer reactions. Similarly, photoreactive polymeric species can be bonded to the surface of the substrate. All of these newly formed covalent bonds increase the durability and stability of the matrix. In cases which generate carbenes and nitrenes, bonds would be formed typically by insertion, hydrogen abstraction to form radicals, rearrangements, etc. This invention is not limited to these mechanisms, and in fact, many mechanisms may be at work within one photoactivatable crosslinker(s) and initiator(s) system.

Photoreactive species are as described herein, and are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet, infrared and visible portions of the spectrum (referred to herein as "photoreactive").

Photoreactive groups respond to external stimuli and undergo active specie generation with the formation of a covalent bond to an adjacent chemical structure, e.g., as provided by the same or a different molecule. Photoreactive groups are those groups of atoms in a molecule that retain their covalent bonds during storage but, upon activation by an external energy source, form covalent bonds with other molecules.

Photoreactive groups generate active species such as free radicals and particularly nitrenes, carbenes, and excited states of ketones upon absorption of electromagnetic energy. Photoreactive groups can be chosen to be responsive to various portions of the electromagnetic spectrum, and photoreactive species that are responsive to electromagnetic radiation, including, but not limited to ultraviolet, infrared and visible portions of the spectrum, are referred to as a "photochemical group" or "photogroup."

The initiators that can be combined with the crosslinkers described herein to form the inventive compositions of the invention include photoreactive initiators as well as thermal initiators.

Free radical initiators can be classified by the following two types.

Type A. Compounds directly produce radicals by unimolecular fragmentation after light absorption. The radicals result from a homolytic or heterolytic cleavage of a sigma bond inside the molecule itself. Common examples include but are not limited to peroxides, and peroxy compounds, benzoin derivatives (including ketoxime esters of benzoin), acetophenone derivatives, benzilketals, α-hydroxyalkylphenones and α-aminoalkylphenones, O-acyl α-oximinoketones, acylphosphine oxides and acylphosphonates, thiobenzoic S-esters, azo and azide compounds, triazines and biimidazoles.

Type B. Compounds generate free radicals by bimolecular hydrogen abstraction after light absorption. The hydrogen abstraction photoreactive group enters an excited state and undergo an intermolecular reaction with a hydrogen donor to generate free radicals. This leads to the formation of a pair of radicals originating from two different molecules. The coupling of radicals can be used to form crosslinks, especially in the solid state in the absence of solvents. Common examples include but are not limited to the following chemical classes. Quinones, benzophenones, xanthones and thioxanthones, ketocoumarins, aromatic 1,2 diketones and phenylglyoxylates. Hydrogen abstraction reactions can also occur intramolecularly. The reactions are not effective for the direct initiation of polymerization and are used internally for the formation of an intermediate. This intermediate may be effective for further cross linking depending on its structure.

The photolysis of organic azides has been shown to result in $N_2$ loss, producing nitrenes as reactive intermediates. Nitrenes are known to undergo five general reactions. 1) Addition to double bonds is observed for both singlet and triplet nitrenes which in the case of arylnitrenes results in rearrangement of the aziridine to a secondary amine as a conceivable mechanism. 2) Insertion of a nitrene into a carbon-hydrogen bond to give a secondary amine which is observed for singlet nitrenes. 3) Hydrogen abstraction is the most common reaction of triplet nitrenes in solution where the formed amino radical and carbon radical generally diffuse apart and the amino radical abstracts a second hydrogen atom to give a primary amine. 4) Nitrene dimerization 5) Attack on heteroatom, for example nitrenes react with azides and oxygen.

Upon direct excitation, carbon halogen bonds such as those in trichloromethyl triazine, tribromomethyl triazine, and aryl iodides, homolytically cleave forming a halogen radical and a carbon radical. Either or both radicals can then abstract hydrogen, disproportionate, couple other radicals, add to unsaturated bonds, or perform other typical radical reactions resulting in crosslinking and bond formation. Suitable examples include trichloromethyl triazines, tribromomethyl triazines and/or aryl iodides.

The use of photoreactive groups in the form of photoreactive aryl ketones are useful such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation wavelengths greater than about 360 nm are useful.

The photoreactive groups of such ketones are preferred since they are readily capable of undergoing an activation/inactivation/reactivation cycle. Benzophenone, acetophenone and anthraquinone are examples of photoreactive moieties, since they are capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone, acetophenone or anthraquinone group is reversible and the molecule returns to ground state energy level upon removal of the energy source. Photoactivatible aryl ketones such as benzophenone, anthraquinone and acetophenone are of particular importance inasmuch as these groups are subject to multiple reactivation in water and hence provide increased coating efficiency.

Another class of photoreactive groups includes compounds having an Si—Si bond, wherein it is believed the Si—Si bond is broken upon excitation with a light source, such as with a laser or UV light. The radicals generated upon the bond breakage provide for reactive sites suitable for use with the present invention. (For examples of Si—Si bond cleavage, see J. Lalevee, M. El-Roz, F. Morlet-Savery, B. Graff, X. Allonas and J. P. Fouassier, "New Highly efficient Radical Photoinitiators based on Si—Si Cleavage" Macromolecules, 2007, 40, 8527-8530 which describes 10,10'-bis (10-phenyl-10H-phenoxasilin (Sigma-Aldrich, St. Louis Mo.) and 9,9'-dimethyl-9,9'-bis-(9H-9-silafluorene, the contents of which are incorporated herein in their entirety.)

Thermal polymerization can be defined as a phenomenon whereby individual substances are joined together to create larger structures by the action of heat. Numerous substances decompose to free radicals when heated. If the decomposition temperature corresponds to a convenient temperature range the substance may be useful in reactions to join small molecules to other small molecules, large molecules to small molecules and large molecules to each other (thermal coupling of polymers), as well as large and small molecules to substrates or particles (thermal bonding to surfaces). Useful thermal initiators include organic peroxides, redox reagents, organic hydroperoxides, azo compounds, metal alkyls and organometallic reagents.

Dialkyl, diacyl and hydrogen peroxides decompose thermally by cleavage of the oxygen bond to yield two alkoxy radicals. Azo compounds decompose thermally to give nitrogen and two alkyl radicals. The radicals may then initiate reactions as described in photopolymerization free radical reactions.

Medical articles that can be fabricated from or coated or treated with the compositions of the invention include, but are not limited to, catheters including urinary catheters and vascular catheters (e.g., peripheral and central vascular catheters), wound drainage tubes, arterial grafts, soft tissue patches, gloves, shunts, stents, tracheal catheters, wound dressings, sutures, guide wires and prosthetic devices (e.g., heart valves and LVADs). Vascular catheters which can be prepared according to the present invention include, but are not limited to, single and multiple lumen central venous catheters, peripherally inserted central venous catheters, emergency infusion catheters, percutaneous sheath introducer systems, thermodilution catheters, including the hubs and ports of such vascular catheters, leads to electronic devices such as pacemakers, defibrillators, artificial hearts, and implanted biosensors.

The superhydrophobic coatings of the invention can be optionally crosslinked through exposure to heat, UV light, electron beam, or gamma-radiation with or without crosslinking agents. Crosslinking agents are chemicals, monomers or polymers having more than one homo- or hetero-functional group, capable of linking two or more binder polymer strands, two or more particles and capable of linking polymer strands and particles to each other and to the surface. In some embodiments of the present invention, the crosslinker has more than one radical generating moiety, such as aryl ketone, azide, peroxide, diazo, carbene or nitrene generator. In other embodiments, the crosslinker has more than one reactive group such as vinyl, carboxy, ester, epoxy, hydroxyl, amido, amino, thio, N-hydroxy succinimide, isocyanate, anhydride, azide, aldehyde, cyanuryl chloride or phosphine that can thermochemically react with functionalized binder polymer. In addition, the superhydrophobic coating can be crosslinked using radical generators. Radicals generators can form new bonds through radical-radical combination, addition to unsaturated bonds, hydrogen abstraction and subsequent recombination, as well as possible electron transfer reactions. Examples of radical initiators include benzophenone, acetophenone derivatives, peroxyides, peroxy compounds, benzoin derivatives, benzilketals, hydroxyalkylphenones and aminoalkylphenones, O-acyl oximoketones, acylphosphin oxides and acylphosphonates, thiobenzoic S-esters, azo and azide compounds, triazines, 1,2 diketones, quinones, coumarins, xanthones.

Suitable crosslinkers include di, tri, tetra, etc. acrylates, methacrylates, vinyl, allyl compounds known in the art.

Exemplary crosslinkers include compounds containing at least two ethylenically unsaturated double bonds. Examples of compounds of this type are N,N'-methylenebisacrylamide, polyethylene glycol diacrylates and polyethylene glycol dimethacrylates each derived from polyethylene glycols having a molecular weight of from 106 to 8500, preferably from 400 to 2000, trimethylolpropane triacrylate, trimethylolpropane trimethacrylate, ethylene glycol diacrylate, ethylene glycol dimethacrylate, propylene glycol diacrylate, propylene glycol dimethacrylate, butanediol diacrylate, butanediol dimethacrylate, hexanediol diacrylate, hexanediol dimethacrylate, allyl methacrylate, diacrylates and dimethacrylates of block copolymers of ethylene oxide and propylene oxide, polyhydric alcohols, such as glycerol or pentaerythritol, doubly or more highly esterified with acrylic acid or methacrylic acid, triallylamine, dialkyldiallylammonium halides such as dimethyldiallylammonium chloride and diethyldiallylammonium chloride, tetraallylethylenediamine, divinylbenzene, diallyl phthalate, polyethylene glycol divinyl ethers of polyethylene glycols having a molecular weight of from 106 to 4 000, trimethylolpropane diallyl ether, butanediol divinyl ether, pentaerythritol triallyl ether, reaction products of 1 mol of ethylene glycol diglycidyl ether or polyethylene glycol diglycidyl ether with 2 mol of pentaerythritol triallyl ether or allyl alcohol, and/or divinylethyleneurea.

Other exemplary crosslinkers include compounds containing at least one polymerizable ethylenically unsaturated group and at least one further functional group. The functional group of these crosslinkers has to be capable of reacting with the functional groups, essentially the acid groups, of the binder polymer. Suitable functional groups include for example hydroxyl, amino, epoxy and aziridino groups. Useful are for example hydroxyalkyl esters of the abovementioned monoethylenically unsaturated carboxylic acids, e.g., 2-hydroxyethyl acrylate, hydroxypropyl acrylate, hydroxybutyl acrylate, hydroxyethyl methacrylate, hydroxypropyl methacrylate and hydroxybutyl methacrylate, allylpiperidinium bromide, N-vinylimidazoles, for example N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. It is also possible to use dialkylaminoethyl acrylate and dimethylaminoethyl methacrylate, diethylaminoethyl acrylate and diethylaminoethyl methacrylate. The basic esters are preferably used in quaternized form or as salt. It is also possible to use glycidyl (meth)acrylate, for example.

Useful crosslinkers further include compounds containing at least two functional groups capable of reacting with the functional groups on the binder polymer for example, acid groups. Suitable functional groups were already mentioned above, i.e., hydroxyl, amino, epoxy, isocyanato, ester, amido and aziridino groups. Examples of such crosslinkers are ethylene glycol, diethylene glycol, triethylene glycol, tetraethylene glycol, polyethylene glycol, glycerol, polyglycerol, triethanolamine, propylene glycol, polypropylene glycol, block copolymers of ethylene oxide and propylene oxide, ethanolamine, sorbitan fatty acid esters, ethoxylated sorbitan fatty acid esters, trimethylolpropane, pentaerythritol, 1,3-butanediol, 1,4-butanediol, polyvinyl alcohol, sorbitol, starch, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, diphenylmethanebis-4,4'-N,N'-diethyleneurea, haloepoxy compounds such as epichlorohydrin and a-methylepifluorohydrin, polyisocyanates such as 2,4-toluoylene diisocyanate and hexamethylene diisocyanate, alkylene carbonates such as 1,3-dioxolan-2-one and 4-methyl-1,3-dioxolan-2-one, also bisoxazolines and oxazolidones, polyamidoamines and also their reaction products with epichlorohydrin, also polyquaternary amines such as condensation products of dimethylamine with epichlorohydrin, homo- and copolymers of diallyldimethylammonium chloride and also homo- and copolymers of dimethylaminoethyl (meth)acrylate which are optionally quaternized with, for example, methyl chloride.

The crosslinkers are present in the appropriate binder for example from 0.001 to 50% by weight, from about 0.01 to about 20%, from about 0.01 to about 5%, from about 0.001 to about 1% by weight.

In certain aspects, the crosslinker includes two or more pendant photoactive groups, described in detail herein, that are free radical generators, nitrene or carbene generators or combinations thereof, and include aryl ketones, azide/nitrene generators, chlorogenerating moieties (a free radical generator), carbene generators or diazo moieties.

The crosslinker can take on various forms, such as those described herein. The crosslinker includes at least two (2) pendant photoactive groups. A general formula for photoactivable crosslinkers comprises:

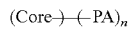

wherein "core" is a linear or branched alkyl group, a linear or branched alkyenyl group, an aryl group, a sugar substrate, a polysaccharide substrate, a peptide, a protein, a nucleic acid, an oligonucleotide, polyacrylics, polyvinyls, nylons, polyurethanes, or polyethers.

Each "PA", independently, is a photoactivatable group that can be an aryl ketone, an azide or nitrene generator, a free radical generator, a carbene generator or a diazo moiety.

"n" is an integer from at least 2 to about 5,000, for example from at least 2 to about 1,000, from at least 2 to about 500, from at least 2 to about 100, including all integers and ranges from at least 2 and 5,000, e.g., from about 3 to about 5,000, from about 4 to about 5,000, from at least 2 to about 4,999, etc.

Additionally, suitable photoactivatable crosslinkers include those described in U.S. Pat. Nos. 5,414,075; 5,637,460; 5,714,360; 6,077,698; and 6,278,018, the contents of which are incorporated herein in their entirety for all purposes and most particularly column 5, line 1 through line 15 and column 8, line 5 through line 30 of U.S. Pat. No. 5,414,075; column 5, line 1 through line 24 and column 8, line 1 through line 20 of U.S. Pat. No. 5,637,460; column 5 through column 8 and column 9, line 1 through line 40 of U.S. Pat. No. 5,714,360; column 7 through column 8 and column 9, line 1 through line 40 of U.S. Pat. No. 6,077,698; column 3 through column 4 and column 5, line 1 through line 28 of U.S. Pat. No. 6,278,018; and column 5, line 1 through line 15 and column 8, line 5 through line 30 of U.S. Pat. No. 5,414,075.

In one aspect, use of photoreactive (photoactive) species as pendent groups within the crosslinkers described herein are generally in the form of photoreactive aryl ketones moieties, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation wavelengths greater than about 360 nm are useful.

The functional groups of ketones are preferred since they are readily capable of undergoing an activation/inactivation/reactivation cycle. Benzophenone is a photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

It should be understood that with reference to a photoreactive moiety, the pendant photoreactive groups include free radical generators, nitrene and carbene generators or combinations thereof, as being part of the crosslinker, that the photoreactive moiety is attached to the remainder of the crosslinker via a bond or a linking group that joins the photoreactive moiety to the remainder of the molecule. In other words, for example, there are benzophenone fragments that are included in the crosslinker, such that the ketone functionality remains.

In one embodiment the crosslinker has the formula:

L-((D-T-C(R$^1$)(XP)CHR$^2$GR$^3$C(=O)R$^4$))$_m$.

L is a linking group. D is O, S, SO, SO$_2$, NR$^5$ or CR$^6$R$^7$. T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond. R$^1$ is a hydrogen atom, an alkyl, alkyloxyalkyl, aryl, aryloxyalkyl or aryloxyaryl group. X is O, S, or NR$^8$R$^9$. P is a hydrogen atom or a protecting group, with the provisio that P is absent when X is NR$^8$R$^9$. R$^2$ is a hydrogen atom, an alkyl, alkyloxyalkyl, aryl, aryloxylalkyl or aryloxyaryl group. G is O, S, SO, SO$_2$, NR$^{10}$, (CH$_2$)$_r$—O— or C=O. R$^3$ and R$^4$ are each independently an alkyl, aryl, arylalkyl, heteroaryl, or a heteroarylalkyl group, or optionally, R$^3$ and R$^4$ can be tethered together via (—CH$_2$—)$_q$, (CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$, (—CH$_2$—)$_r$S(O)$_2$(—CH$_2$—)$_s$, or (—CH$_2$—)$_r$NR(—CH$_2$—)$_s$. R$^5$ and R$^{10}$ are each independently a hydrogen atom or an alkyl, aryl, or arylalkyl group. R$^6$ and R$^7$ are each independently a hydrogen atom, an alkyl, aryl, arylalkyl, heteroaryl or heteroarylalkyl group. R$^8$ and R$^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one aspect, L is a branched or unbranched alkyl chain having between about 2 and about 10 carbon atoms.

In another aspect, D is an oxygen atom (O).

In still another aspect, T is (—CH$_2$—)$_x$ or (—CH$_2$CH$_2$—O—)$_x$ and x is 1 or 2.

In still yet another aspect, R$^1$ is a hydrogen atom.

In yet another aspect, X is an oxygen atom, O, and P is a hydrogen atom.

In another aspect, R$^2$ is a hydrogen atom.

In still another aspect, G is an oxygen atom, O.

In still yet another aspect, R$^3$ and R$^4$ are each individually aryl groups, which can be further substituted, and m is 3.

In one particular aspect, L is

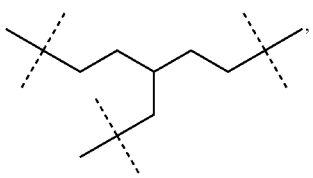

D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 3 and x is 1.

In yet another particular aspect, L is (—CH$_2$—)$_y$, D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 2, x is 1 and y is an integer from 2 to about 6, and in particular, y is 2, 4 or 6.

In certain embodiments, x is an integer from about 1 to about 500, more particularly from about 1 to about 400, from about 1 to about 250, from about 1 to about 200, from about 1 to about 150, from about 1 to about 100, from about 1 to about 50, from about 1 to about 25 or from about 1 to about 10

In another embodiment, the crosslinker has the formula:

L-((T-C(R$^1$)(XP)CHR$^2$GR$^3$C(=O)R$^4$))$_m$.

wherein L, T, R$^1$, X, P, R$^2$, G, R$^3$, R$^4$, R$^8$, R$^9$, R$^{10}$, R, q, r, s, m, t and x are as defined above.

In one aspect, L has a formula according to structure (I):

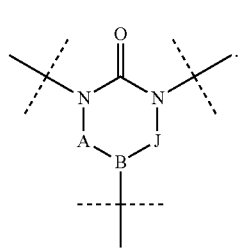

(I)

A and J are each independently a hydrogen atom, an alkyl group, an aryl group, or together with B form a cyclic ring, provided when A and J are each independently a hydrogen atom, an alkyl group, or an aryl group then B is not present, B is NR$^{11}$, O, or (—CH$_2$—)$_z$, provided when A, B and J form a ring, then A and J are (—CH$_2$—)$_z$ or C=O, R$^{11}$ is a hydrogen atom, an alkyl group, an aryl group or denotes a bond with T, each z independently is an integer from 0 to 3 and provided when either A or J is C=O, then B is NR$^{11}$, O, or (—CH$_2$—)$_z$ and z must be at least 1.

In another aspect T is —CH$_2$—.

In another embodiment, the family has the formula:

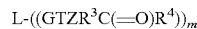
L-((GTZR$^3$C(=O)R$^4$))$_m$ wherein L, T, G, R$^3$, R$^4$, R$^{10}$, R, q, r, s, m, t and x are as defined above. Z can be a C=O, COO or CONH when T is (—CH$_2$—)$_x$.

In one aspect, L has a formula according to structure (I):

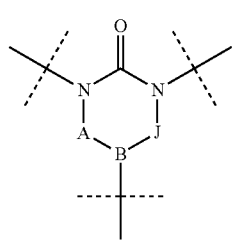

(I)

wherein A, B, J, R$^{11}$, and z are as defined above.

In another aspect, L has a formula according to structure (II):

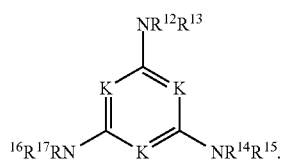

(II)

R$^{12}$, R$^{13}$, R$^{14}$, R$^{15}$, R$^{16}$, R$^{17}$ are each independently a hydrogen atom, an alkyl or aryl group or denotes a bond with T, provided at least two of R$^{12}$, R$^{13}$, R$^{14}$, R$^{15}$, R$^{16}$, R$^{17}$ are bonded with T and each K, independently is CH or N.

In another embodiment, the crosslinker has the formula:

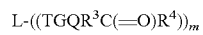
L-((TGQR$^3$C(=O)R$^4$))$_m$ wherein L, G, R$^3$, R$^4$, R$^{10}$, R, q, r, s, m, t and x are as defined above. T is (—CH$_2$—)—, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond. Q is (—CH$_2$—)$_p$, (—CH$_2$CH$_2$—O—)$_p$, (—CH$_2$CH$_2$CH$_2$—O—)$_p$ or (—CH$_2$CH$_2$CH$_2$CH$_2$—O—)$_p$ and p is an integer from 1 to about 10.

In one aspect, L has a formula according to structure (I):

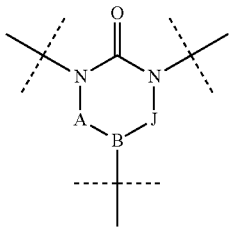

(I)

wherein A, B, J, R$^{11}$, and z are as defined above.

In another aspect, L has a formula according to structure (II):

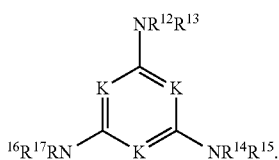

(II)

R$^{12}$, R$^{13}$, R$^{14}$, R$^{15}$, R$^{16}$, R$^{17}$ are each independently a hydrogen atom, an alkyl or aryl group or denotes a bond with T, provided at least two of R$^{12}$, R$^{13}$, R$^{14}$, R$^{15}$, R$^{16}$, R$^{17}$ are bonded with T and each K, independently is CH or N.

In still yet another aspect, compounds of the present invention provide that R$^3$ and R$^4$ are both phenyl groups and are tethered together via a CO, a S or a CH$_2$.

In yet another aspect, compounds of the present invention provide when R$^3$ and R$^4$ are phenyl groups, the phenyl groups can each independently be substituted with at least one alkyloxyalkyl group, such as CH$_3$O—(CH$_2$CH$_2$O—)$_n$—, or CH$_3$O(—CH$_2$CH$_2$CH$_2$O—)$_n$-a hydroxylated alkoxy group, such as HO—CH$_2$CH$_2$O—, HO(—CH$_2$CH$_2$O—)$_n$— or HO(—CH$_2$CH$_2$CH$_2$O—)$_n$—, etc. wherein n is an integer from 1 to about 10.

In another embodiment the crosslinker has the formula:

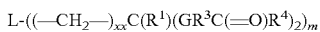

wherein L, each R, R$^1$, each G, each R$^3$, each R$^4$, each R$^{10}$, each q, each r, each s, each t and m are as defined above and xx is an integer from 1 to about 10.

In one aspect, L has a formula according to structure (I):

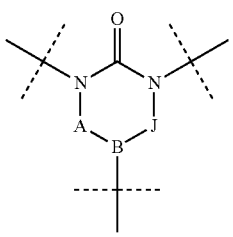

(I)

wherein A, B, J, R$^{11}$, and z are as defined above.

In another aspect, A and B are both hydrogen atoms.

In still another aspect, xx is 1.

In yet another aspect, R$^1$ is H.

In still yet another aspect, G is (—CH$_2$—)$_t$O— and t is 1.

In another aspect, R$^3$ and R$^4$ are each individually aryl groups.

In still yet another embodiment, xx is 1, R$^1$ is H, each G is (—CH$_2$—)$_t$O—, t is 1 and each of R$^3$ and R$^4$ are each individually aryl groups.

In another embodiment, the crosslinker has the formula

where L, R, R$^1$, R$^2$, R$^3$, R$^4$, R$^8$, R$^9$, R$^{10}$, X, P, G, q, r, s, t, and m are as defined above.

In one aspect, L is

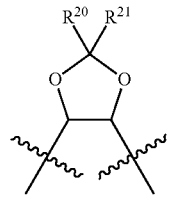

and R$^{20}$ and R$^{21}$ are each individually a hydrogen atom, an alkyl group or an aryl group.

In another aspect, R$^1$ is H.

In still another aspect, wherein X is O.

In yet another aspect, P is H.

In still yet another aspect, R$^2$ is H.

In another aspect, G is (—CH$_2$—)tO— and t is 1.

In still another aspect, R$^3$ and R$^4$ are each individually aryl groups.

In yet another aspect, R$^1$ is H, X is O, P is H, R$^2$ is H, G is (—CH$_2$—)$_t$O—, t is 1, R$^3$ and R$^4$ are each individually aryl groups and R$^{20}$ and R$^{21}$ are both methyl groups.

In yet another embodiment, the crosslinker has the formula:

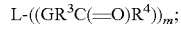

where L, G, R, R$^3$, R$^4$, R$^{10}$, q, r, s, m and t are as defined above.

In one aspect, L is

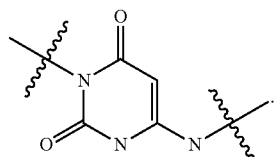 [SMILES: *Nc1cc(=O)n(*)c(=O)[nH]1]

In another aspect, G is C═O.

In still another aspect, R$^3$ and R$^4$ are each individually aryl groups.

In yet another aspect, G is C═O and R$^3$ and R$^4$ are each individually aryl groups.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyloxyalkyl" refers to a moiety having two alkyl groups tethered together via an oxygen bond. Suitable alkyloxyalkyl groups include polyoxyalkylenes, such as polyethyleneoxides, polypropyleneoxides, etc. that are terminated with an alkyl group, such as a methyl group. A general formula for such compounds can be depicted as R'—(OR")$_n$ or (R'O)$_n$—R" wherein n is an integer from 1 to about 10, and R' and R" are alkyl or alkylene groups.

"Alkenyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group having from 1 to 6 carbon atoms. In preferred embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryloxyalkyl" refers to a moiety having an aryl group and an alkyl group tethered together via an oxygen bond. Suitable aryloxyalkyl groups include phenyloxyalkylenes, such as methoxyphenyl, ethoxyphenyl, etc.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cycloalkenyl; cyclohexyls such as cyclohexanyl and cyclohexenyl; and the like.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, benzoxazine, benzimidazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Leaving group" is a group that is displaced during a reaction by a nucleophilic reagent. Suitable leaving groups include S(O)$_2$Me, —SMe or halo (e.g., F, Cl, Br, I).

"Linking group" is a group that serves as an intermediate locus between two or more end groups. The nature of the linking group can vary widely, and can include virtually any combination of atoms or groups useful for spacing one molecular moiety from another. For example, the linker may be an acyclic hydrocarbon bridge (e.g. a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

"Protecting group" is a group that is appended to, for example, a hydroxyl oxygen in place of a labile hydrogen atom. Suitable hydroxyl protecting group(s) include esters (acetate, ethylacetate), ethers (methyl, ethyl), ethoxylated derivatives (ethylene glycol, propylene glycol) and the like that can be removed under either acidic or basic conditions so that the protecting group is removed and replaced with a hydrogen atom. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

It should be understood that the compositions of the invention (the combination of the crosslinker and initiator) can be combined immediately prior to use. Alternatively, the components can be prepared separately, for example as solutions, and then combined prior to use. In yet another aspect, the components can be prepared and placed in separate containers, thus providing a two component kit. Alternatively, the components can be mixed and stored in a single container suitable for use.

The compositions of the invention can be used as coating agents.

The compositions of the invention can be applied to a surface of interest in any suitable manner. For example, the composition can be applied by dip coating or by dispersing the compound on the surface (for example, by spray coating). Suitable methods of application include application in solution, dipping, spray coating, knife coating, and roller coating. In one aspect, the composition is applied to the surface via spray coating, as this application method provides increased density of the coating on the support surface, thereby improving durability.

Crosslinkers encompassed by the present invention can be prepared by a variety of methods. Generally, the core molecule has functionalities that can react with or be converted into more than one aryl ketone, azide, diazo or trichloromethyl triazine moieties. This can be accomplished by nucleophilic displacement of a suitable leaving group on either the core molecule or the photoactivatable agent. For example, hydroxyl groups of the core molecule can be converted into a suitable leaving group such as a halide and subjected to nucleophilic displacement by sodium azide. Similarly, a halogenated site can be converted into an amine that is then suitable for conversion to a diazo moiety. Carbene generation can be accomplished by uv irradiation of diazo and azide compounds. Trichloromethyl triazine moiety can be incorporated into a core molecule by first preparing the acyl chloride of 4-(4-carboxyphenyl)-2,6-bis(trichloromethyl)-s-triazine with thionyl chloride followed by reaction with a suitable nucleophilic agent on the core molecule.

Aryl ketone containing crosslinkers encompassed by the present invention can be prepared by selection of an appropriate aryl group with a photoactivatable group and at least one group that can either act as a nucleophilic site or can be acted upon in a nucleophilic displacement reaction with a linking agent (L) having at least two opposing groups, either a leaving group(s) or a nucleophilic group(s). General synthetic schemes detailed below demonstrate two approaches suitable to prepare compounds of the invention.

Scheme I

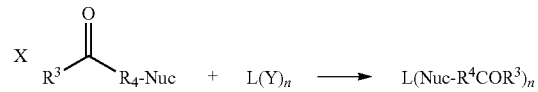

or

Scheme II

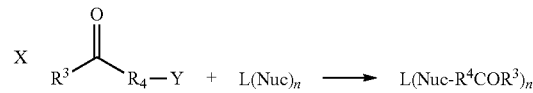

wherein X is an integer equivalent to "n" and n is an integer between 2 and about 6, $R^3$ and $R^4$ are as defined above, "Y" is a leaving group or a group that can be acted upon by a nucleophilic group, such as an ester, carboxylic acid halide, etc. and "Nuc" is a nucleophilic group, as described in further detail below. Alternatively, the reaction between "Y" and "Nuc" can be a condensation reaction, such as the reaction between, for example, a hydroxyl group and a carboxylic acid.

It should be understood in schemes I and II, that $R^3$ and $R^4$ are interchangeable.

Suitable nucleophilic groups (Nuc) include, for example, amines, hydroxyl, thiol, etc.

Suitable leaving groups, or groups susceptible to nucleophilic attack, include esters, ethers, epoxides, halides, isocyanates, isothiocyanates, sulfonyl chlorides, anhydrides, carboxylic acid halides, carboxylic acid esters, and aldehydes.

Resultant functional moieties from the reaction between the nucleophilic group and leaving (or condensation group) include, for example, esters, ethers, carbamates, thiocarbamates, sulfones, amides, ureas, thiourea, amines, sulfonamides, imines (that can be further reduced with a reducing agent such as sodium borohydride to an amine), etc.

Suitable reaction conditions for such condensations or nucleophilic displacements are known in the art. For example, hydroxyl containing moieties can be condensed with a carboxylic acid under dehydrating conditions (refluxing toluene, acid catalyst, Dean Stark trap) to form esters. Reactive halides can be displaced by hydroxyl groups under basic conditions. An isocyanate reacts with a hydroxyl group with heat to form carbamates. Likewise, an isothiocyanates reacts with a hydroxyl group to form a thiocarbamate. Under deprotonation conditions, a hydroxide ion reacts with an epoxide to form an ether linkage and forming a new hydroxyl group. Reaction between a hydroxyl and a sulfonyl chloride forms a sulfone. Reaction between a hydroxyl and an anhydride will form a ester with a carboxylic acid portion as well.

Reaction between a hydroxyl group and an ester will also form an ester, with the removal of a corresponding displaced alcohol, generally under conditions that drive off the displaced alcohol.

Much like the reactions with hydroxyl groups, amines serve in similar manner. For example, an amine can react with an activated carboxylic acid for form an amide. Activation of a carboxylic acid can be facilitated by various methods in the art, including for example, use of dicyclohexylcarbodiimide (DCC) that generates urea as a side product. An isocyanate reacts with an amine to form a urea and an isothiocyanate reacts with an amine to form a thiourea.

Selection of appropriate reaction conditions can provide a product that includes a majority of fully substituted and desired crosslinking material.

It should also be understood that each "Y" independently can be different. Therefore, it is possible to have reaction products that include an ether linkage as well as an ester linkage to the carbonyl containing photoactivatable group.

An exemplary non-limiting reaction is depicted in Scheme I, in which a hydroxyl group undergoes nucleophilic addition to an ester or acid halide or can undergo a condensation reaction between the hydroxyl group and a carboxylic acid.

Scheme I

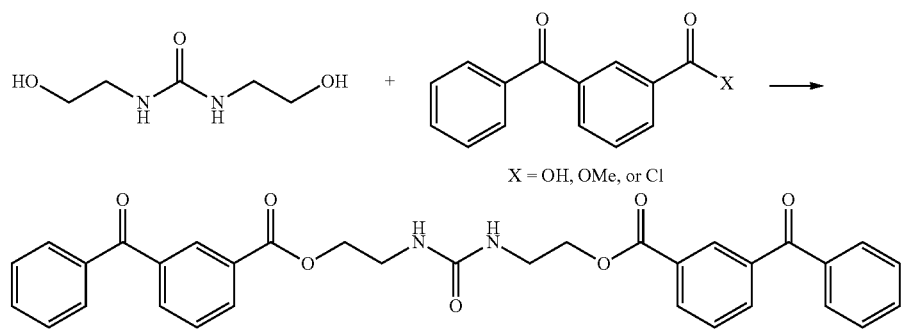

X = OH, OMe, or Cl

Reaction between an amine and an epoxide will form an amine with an appended hydroxyl group from the nucleophilic displacement of the epoxide ring. Reaction between an amine and a sulfonyl chloride will form a sulfonamide. Reaction between an anhydride and an amine will afford an amide with a carboxylic portion attached to the product. Reaction between an aldehyde and an amine will form an imine which can be further reduced to an amine. Reaction between a carboxylic acid halide and an amine will form an amide, as well as the reaction between a carboxylic ester and amine. Lastly, melamine type compounds can react with an amine to form amine linkages.

Reaction conditions to form the compounds of the invention are known in the art. For example, suitable reaction conditions are described in "March's Advanced Organic Chemistry Reactions, Mechanisms, and Structure, 5th Edition, John Wiley & Sons, Michael B. Smith & Jerry March; Fieser and Fieser's Reagents for Organic Synthesis" John Wiley & Sons, NY; Vogel's Textbook of Practical Organic Chemistry (Fifth Edition) by A. I. Vogel, B. S. Furniss, A. J. Hannaford, P. W. G. Smith, and A. R. Tatchell, Longman Scientific and Technical, Longman Group UK; and Advanced Organic Chemistry parts A and B" Third Edition, F. A. Carey, R. S. Sundberg, Plenum Press, NY, 1990, the contents of which are incorporated herein by reference in their entirety.

It should be understood that the reaction products of the crosslinkers can be isolated an purified by suitable methods known in the art. These include, but are not limited to, crystallization, distillation, chromatography, etc. and purities of the crosslinkers can be greater than 80%, in particular greater than 90%, more particularly greater than 95% and most particularly greater than 99%, e.g., 99.5% or greater.

It should also be understood that where mixtures of products (mono, di, tri-substituted, etc.) can be formed during the synthetic process, that the mixture can be separated and purified to afford a crosslinker that has the purities noted above.

In another aspect, the present invention provides a bilayer coating that includes a first layer having a bioactive agent and a second layer comprising a hydrophobic binder and a plurality of particles comprising a size between about 1 nm to about 25 microns. In one aspect, the particles are dispersed throughout the bulk of the second layer.

In another aspect, the present invention provides a coating that includes a bioactive agent encapsulated in a first polymeric binder, a second hydrophobic binder, and a plurality of particles comprising a size between about 1 nm to about 25 microns, wherein the encapsulated bioactive agent and plurality of particles are dispersed throughout the bulk of the second layer.

In still another aspect, the present invention provides a coating comprising a hydrophobic binder over a substrate impregnated with a bioactive agent. The substrate may be the surface of a device, for example a catheter or stent, wherein the bioactive agent is located.

The following paragraphs enumerated consecutively from 1 (one) through 63 (sixty three) provide for various aspects of the present invention. In one embodiment, in a first paragraph (1), the present invention provides a coating comprising:
a first hydrophobic binder;
a plurality of particles comprising a size between about 1 nm to about 25 microns; and a
bioactive agent.

2. The coating of paragraph 1, wherein the particles are dispersed throughout the bulk of the coating.

3. The coating of either of paragraphs 1 or 2, further comprising a crosslinker.

4. The coating of either of paragraphs 1 or 2, further comprising an initiator.

5. The coating of either of paragraphs 1 or 2, further comprising a crosslinker and an initiator.

6. The coating of any of paragraphs 1 through 5, wherein the hydrophobic polymeric binder has a surface tension of less than about 50 mN/m.

7. The coating of paragraph 6, wherein the hydrophobic binder is hydrophobic polymer that is a homopolymer or copolymer of a polyalkylene, a polyacrylate, a polymethacrylate, a polyester, a polyamide, a polyurethane, a polyvinylarylene, a polyvinyl ester, a polyvinylarylene/alkylene copolymer, a polyalkyleneoxide, a polyvinyl halide, or mixtures thereof.

8. The coating of either of paragraphs 3 or 5, wherein the crosslinker has more than one acrylate, methacrylate, vinyl or diarylketone containing moiety.

9. The coating of either of paragraphs 4 or 5, wherein the initiator is benzophenone, an acetophenone derivative, a peroxide, a peroxy compound, a benzoin derivative, a benzilketal, a hydroxyalkylphenone, an aminoalkylphenone, an O-acyl oximoketone, an acylphosphine oxides, an acylphosphonate, a thiobenzoic S-ester, an azo or azide compound, a triazine, a 1,2 diketone, a quinone, a coumarins, a xanthone, azobis-isobutyronitrile or a mixture thereof.

10. The coating of any of paragraphs 1 through 9, wherein the particles are aluminum oxides (alumina), titanium oxide, zirconium oxide, gold (treated with organo thiols), silver (organo thiol or silane treated), nickel, nickel oxide, iron oxide, and alloys (all treated with silane), polystyrene particles, (meth)acrylates particles, PTFE particles, silica particles, polyolefin particles, polycarbonate particles, polysiloxane particles, silicone particles, polyester particles, polyamide particles, polyurethane particles, ethylenically unsaturated polymer particles, polyanhydride particles and biodegradable particles such as polycaprolactone (PCL) and polylactideglycolide (PLGA), and nanofibers, nanotubes, or nanowires, or combinations thereof.

11. The coating of any of paragraphs 1 through 10, wherein the particles can be silanized.

12. The coating of any of paragraphs 1 through 11, wherein the bioactive agent is an anti-inflammatory, an antimicrobial or an antibiotic.

13. The coating of any of paragraphs 1 through 12, wherein the bioactive agent is encapsulated within a second binder prior to incorporation into the first hydrophobic binder, wherein the first and second binders can be the same or different, provided the first binder is hydrophobic.

14. A composite comprising:
a substrate; and
the coating of any of paragraphs 1 through 13 coated onto the substrate.

15. A drug eluting medical device comprising:
a medical device; and
the coating of any of paragraphs 1 through 13 coated onto the medical device.

16. A bilayer coating comprising;
a first layer comprising a bioactive agent; and
a second layer comprising a hydrophobic binder and a plurality of particles comprising a size between about 1 nm to about 25 microns.

17. The bilayer coating of paragraph 16, wherein the particles are dispersed throughout the bulk of the second layer.

18. The bilayer coating of either of paragraphs 16 or 17, wherein the second layer further comprises a crosslinker.

19. The bilayer coating of either of paragraphs 16 or 17, wherein the second layer further comprises an initiator.

20. The bilayer coating of either of paragraphs 16 or 17, wherein the second layer further comprises a crosslinker and an initiator.

21. The bilayer coating of either of paragraphs 16 or 17, wherein the first layer further comprises a binder.

22. The bilayer coating of paragraph 21, wherein the first layer binder is hydrophilic.

23. The bilayer coating of paragraph 21, wherein the first layer binder is hydrophobic.

24. The bilayer coating of any of paragraphs 21 through 23, wherein the first layer further comprises a crosslinker.

25. The bilayer coating of any of paragraphs 21 through 23, wherein the first layer further comprises an initiator.

26. The bilayer coating of any of paragraphs 21 through 23, wherein the first layer further comprises a crosslinker and an initiator.

27. The bilayer coating of any of paragraphs 16 through 26, wherein the hydrophobic polymeric binder has a surface tension of less than about 50 mN/m.

28. The bilayer coating of paragraph 27, wherein the hydrophobic binder is hydrophobic polymer that is a homopolymer or copolymer of a polyalkylene, a polyacrylate, a polymethacrylate, a polyester, a polyamide, a polyurethane, a polyvinylarylene, a polyvinyl ester, a polyvinylarylene/alkylene copolymer, a polyalkyleneoxide, a polyvinyl halide, or mixtures thereof.

29. The bilayer coating of any of paragraphs 18, 20, 24 or 26, wherein the crosslinker is a diacrylate, dimethacrylate, divinyl or a diarylketone containing moiety.

30. The bilayer coating of any of paragraphs 19, 20, 25 or 26, wherein the initiator is benzophenone, an acetophenone derivative, a peroxide, a peroxy compound, a benzoin derivative, a benzilketal, a hydroxyalkylphenone, an aminoalkylphenone, an O-acyl oximoketone, an acylphosphine oxides, an acylphosphonate, a thiobenzoic S-ester, an azo or azide compound, a triazine, a 1,2 diketone, a quinone, a coumarins, a xanthone, azobis-isobutyronitrile, or a mixture thereof.

31. The bilayer coating of any of paragraphs 16 through 30, wherein the particles are aluminum oxides (alumina), titanium oxide, zirconium oxide, gold (treated with organo thiols), silver (organo thiol or silane treated), nickel, nickel oxide, iron oxide, and alloys (all treated with silane), polystyrene particles, (meth)acrylates particles, PTFE particles, silica particles, polyolefin particles, polycarbonate particles, polysiloxane particles, silicone particles, polyester particles, polyamide particles, polyurethane particles, ethylenically unsaturated polymer particles, polyanhydride particles and biodegradable particles such as polycaprolactone (PCL) and polylactideglycolide (PLGA), and nanofibers, nanotubes, or nanowires, or combinations thereof.

32. The bilayer coating of any of paragraphs 16 through 31, wherein the particles can be silanized.

33. The bilayer coating of any of paragraphs 16 through 32, wherein the bioactive agent is an anti-inflammatory, an antimicrobial or an antibiotic.

34. The bilayer coating of paragraph 21, wherein the first and second binders can be the same or different, provided the second binder is hydrophobic.

35. A composite comprising:
a substrate; and
the bilayer coating of any of paragraphs 16 through 34 coated onto the substrate.

36. A drug eluting medical device comprising:
a medical device; and
the bilayer coating of any of paragraphs 16 through 34 coated onto the medical device.

37. A method to provide drug eluting capability to a substrate comprising the step:
treating a substrate with the coating of any of paragraphs 1 through 15 to provide a coating with drug eluting capability.

38. A method to provide drug eluting capability to a medical device comprising the step:

treating a medical device with the coating of any of paragraphs 1 through 15 to provide a coating with drug eluting capability.

39. A method to provide drug eluting capability to a substrate comprising the steps:
treating a substrate with the first layer of any of paragraphs 16 through 34 and subsequently treating the first layer with the second layer of any of paragraphs 16 through 34 to provide drug eluting capability.

40. A method to provide drug eluting capability to a medical device comprising the steps:
treating a medical with the first layer of any of paragraphs 16 through 34 and subsequently treating the first layer with the second layer of any of paragraphs 16 through 34 to provide drug eluting capability.

41. The coating, composite, device or method of any of paragraphs 1 through 40, further comprising treatment with ionizing radiation.

42. A coating comprising;
a bioactive agent encapsulated in a first polymeric binder;
a second hydrophobic binder; and
a plurality of particles comprising a size between about 1 nm to about 25 microns, wherein the encapsulated bioactive agent and plurality of particles are dispersed throughout the bulk of the second layer.

43. The coating of paragraph 42, wherein the second binder further comprises a crosslinker.

44. The coating of paragraph 42, wherein the second binder further comprises an initiator.

45. The coating of paragraph 42, wherein the second binder further comprises a crosslinker and an initiator.

46. The coating of any of paragraphs 42 through 45, wherein the first binder is hydrophilic.

47. The coating of any of paragraphs 42 through 45, wherein the first binder is hydrophobic.

48. The coating of any of paragraphs 42 through 47, wherein the first binder further comprises a crosslinker.

49. The coating of any of paragraphs 42 through 47, wherein the first binder further comprises an initiator.

50. The coating of any of paragraphs 42 through 47, wherein the first binder further comprises a crosslinker and an initiator.

51. The coating of any of paragraphs 42 through 50, wherein the hydrophobic polymeric binder has a surface tension of less than about 50 mN/m.

52. The coating of paragraph 51, wherein the hydrophobic binder is hydrophobic polymer that is a homopolymer or copolymer of a polyalkylene, a polyacrylate, a polymethacrylate, a polyester, a polyamide, a polyurethane, a polyvinylarylene, a polyvinyl ester, a polyvinylarylene/alkylene copolymer, a polyalkyleneoxide, a polyvinyl halide, or mixtures thereof.

53. The coating of any of paragraphs 43, 45, 48 or 50, wherein the crosslinker is a diacrylate, dimethacrylate, divinyl or a diarylketone containing moiety.

54. The coating of any of paragraphs 44, 45, 49 or 50, wherein the initiator is benzophenone, an acetophenone derivative, a peroxide, a peroxy compound, a benzoin derivative, a benzilketal, a hydroxyalkylphenone, an aminoalkylphenone, an O-acyl oximoketone, an acylphosphine oxides, an acylphosphonate, a thiobenzoic S-ester, an azo or azide compound, a triazine, a 1,2 diketone, a quinone, a coumarins, a xanthone, azobis-isobutyronitrile or a mixture thereof.

55. The coating of any of paragraphs 42 through 54, wherein the particles are aluminum oxides (alumina), titanium oxide, zirconium oxide, gold (treated with organo thiols), silver (organo thiol or silane treated), nickel, nickel oxide, iron oxide, and alloys (all treated with silane), polystyrene particles, (meth)acrylates particles, PTFE particles, silica particles, polyolefin particles, polycarbonate particles, polysiloxane particles, silicone particles, polyester particles, polyamide particles, polyurethane particles, ethylenically unsaturated polymer particles, polyanhydride particles and biodegradable particles such as polycaprolactone (PCL) and polylactideglycolide (PLGA), and nanofibers, nanotubes, or nanowires, or combinations thereof.

56. The coating of any of paragraphs 42 through 55, wherein the particles can be silanized.

57. The coating of any of paragraphs 42 through 56, wherein the bioactive agent is an anti-inflammatory, antimicrobial or an antibiotic.

58. The bilayer coating of paragraph 57, wherein the first and second binders can be the same or different, provided the second binder is hydrophobic.

59. A composite comprising:
a substrate; and
the coating of any of paragraphs 42 through 58 coated onto the substrate.

60. A drug eluting medical device comprising:
a medical device; and
the coating of any of paragraphs 42 through 58 coated onto the medical device.

61. A method to provide drug eluting capability to a substrate comprising the steps:
encapsulating a bioactive agent in a first polymeric binder;
mixing the encapsulated binder with a second hydrophobic polymeric binder, resulting in a coating mixture; and
treating a substrate with the coating mixture of any of paragraphs 42 through 58 to provide drug eluting capability.

62. A method to provide drug eluting capability to a medical device comprising the steps:
encapsulating a bioactive agent in a first polymeric binder;
mixing the encapsulated binder with a second hydrophobic polymeric binder, resulting in a coating mixture; and
treating a medical device with the coating mixture of any of paragraphs 42 through 58 to provide drug eluting capability.

63. The coating, composite, device or method of any of paragraphs 42 through 62, further comprising treatment with ionizing radiation.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Photocrosslinker A Synthesis 1.2 g (4 mmol) of triglycidyl isocyanurate (Aldrich Chemicals, Milwaukee, Wis.) and 2.4 g (12 mmol) of 4-hydroxybenzophenone (Aldrich Chemicals, Milwaukee, Wis.) were mixed in a 50-ml round bottom flask containing a magnetic stir bar. The flask was flushed with argon for 10 min and heated to 130° C. in an oil bath. Once the reaction mixture melted, 6 mg (0.02 mmol) of triphenylphosphine (Aldrich Chemicals, Milwaukee, Wis.) was added. The mixture was stirred for another 2 minutes under argon and cooled to room temperature. The reaction residue was dissolved in 30 ml chloroform, then washed with 4N NaOH (30 ml×3) and deionized water (30 ml×3). The organic layer was dried over magnesium sulfate and concentrated to dryness on the under reduced pressure. The product was purified by column chromatography (silica gel, 230-400 mesh, Whatman, Inc.) using ethyl acetate as eluent ($R_f$~4.5). The fractions containing the pure product were combined and concentrated under reduced pressure and a white powder was obtained after drying under vacuum (yield 70%).

The crosslinker (Photocrosslinker A) is soluble in most common solvents including chloroform, methylene chloride, acetone, ethyl acetate, isopropanol, etc. $_1$H NMR ($CDCl_3$) confirmed the structure of the product. The peaks at d 7.78 ppm (m, 12H), 7.46 ppm (m, 9H), 6.98 ppm (m, 6H) were the typical signals from 4-substituted benzophenone. The peak at d 4.35 ppm (m, 6H) was assigned to the protons of methylene connected to phenoxy group. The peak at d 4.13 ppm (m, 9H) was a combination of 6 protons of 3 methylene groups connected to nitrogen atom and 3 protons from 3 methine groups. The peak at d 3.00 ppm (s, 3H) corresponded to hydroxyl groups. This material is referred to as "Photocrosslinker A".

Example 2

Chlorhexidine Elution into Deionized Water from a Superhydrophobic Sample

Sample Preparation

PVC slides (Rinzl brand, VWR, Batavia, Ill., 0.5 mm thick) were cut into 55×12 mm sections, cleaned with IPA, and dried overnight in a vacuum oven (40° C.). A basecoat solution, containing 14 mg/ml chlorhexidine (Sigma Aldrich, St. Louis, Mich.) and 20 mg/ml polycaprolactone, PCL, (~80K g/mol) (Aldrich Chemical Co. Milwaukee, Wis.) dissolved in methyl acetate, was applied to the slides by a dipcoat method. The slides were dipped into the basecoat solution and after a 30 sec dwell, the slides were withdrawn at a rate 5 cm/sec. The coated slides were air dried and then dried overnight in a vacuum oven (40° C.). The samples were weighed prior to application of the basecoat, and reweighed following oven drying of the basecoat. A superhydrophobic surface coating was then applied to the sample, covering the chlorhexidine/polycaprolactone basecoat. The superhydrophobic topcoat solution consisted of 15 mg/mL PVC (97k g/mol) (Aldrich Chemical Co. Milwaukee, Wis.), 5 mg/mL PCL, 24 mg/mL LE3 particles (Evonik Industries, Essen, Germany) and 0.8 mg/mL Photocrosslinker A, dissolved in tetrahydrofuran. The superhydrophobic surface coating solution was applied by spray-coating from a nanoparticle suspension, followed by air drying and illumination with UV lamp (5 min, 200-400 nm, Harland Medical UVM400, Eden Prairie, Minn.). The superhydrophobic coated slides were vacuum oven dried overnight at (40° C.). The superhydrophobicity of the surface coating was verified visually by an initial inability of the surface to wet, when submerged in water for drug elution studies.

Bioactive Agent Release Assay

Coated slides were submerged in 22 mL deionized water at room temperature. At various time intervals, the solution was exchanged for fresh deionized water and the chlorhexidine content was quantified by spectrophotometric absorbance at 254 nm, and confirmed at the end of the experiment by drying and weighing eluted samples on a micro-balance. The drug release curve for 21 days of elution is shown in FIG. 1.

Flexibility and Durability No damage to the coating (ie cracking or delamination) of samples was observed visually following repeated flexion of superhydrophobic coated slides to 90 degree angles. Furthermore, no visual damage or loss of superhydrophobicity was found following durability testing (80 A durometer, 100 gm force, 10 pulls).

Example 3

Microbial Zone of Inhibition for Superhydrophobic/Drug Eluting Surfaces

Two superhydrophobic coated polyvinyl slides containing chlorhexidine were prepared as described in example 1, except that the topcoat contained 20 mg/mL PCL, 24 mg/mL LE3 particles and 0.8 mg/mL Photocrosslinker A, and it was dissolved in methyl acetate instead of tetrahydrofuran. One coated slide was stored dry in an amber capped vial and the second coated slide underwent the bioactive agent release assay for 14 days as described in example 1. After 14 days, the coated slide was dried in vacuum oven at 40° C. overnight.

A 1.8 mL suspension of *Staphylococcus aureus* ATCC#6538 (Microbiologics, St. Cloud Minn.) (approximately $10^8$ CFU/mL which corresponds to a McFarland Nephelometer 0.5) was prepared in 1×PBS using a sterile swab, a small borosilicate test tube (12×75 mm), and a Vitek colorimeter. In order to ensure that the coatings were neither over challenged nor under challenged, inoculum counts were performed. The original organism suspension (~$10^8$) was diluted 10-fold, 100-fold, and finally 1000-fold. The resulting organism suspension density was approximately $10^3$. 100 µL of the $10^3$ suspension was spread plated to 100 mm Mueller-Hinton agar (resulting in a $10^2$ countable plate).

Within a biological safety cabinet, 170 mm Mueller-Hinton plates were lawned with the *S. aureus* McFarland Nephelometer 0.5 suspension via sterile swab (lawn, turn the plate 60°, lawn again, turn the plate 60°, lawn once more, and drag the swab around the perimeter of the plate).

The two coated PVC slides were placed on separate plates on the agar surface via sterile forceps. The plates were then inverted and incubated at 37° C. for 18 hours. Upon removal from incubation, zones of inhibition were measured. (See Table 1 below). Because the zones of inhibition were not uniform, 16 measurements were taken: 7 on each long side of the coupon and 2 on the short coated end. The 16 measurements were averaged to obtain one figure that was applicable to the entire zone of inhibition.

Additionally negative controls were performed. To ensure that the PVC slide itself was not antimicrobial, an uncoated coupon was subjected to Kirby-Bauer testing. To ensure that the coating on the coupons was not antimicrobial, a coupon was coated with a formulation that did not include chlorhexidine and was subjected Kirby-Bauer testing.

Inoculum count plates: Plate 1=196 CFU/plate, Plate 2=261 CFU/plate. Average of Plate 1 & Plate 2: 228.5 CFU/plate.

Based on the inoculum count results, the McFarland Nephelometer 0.5 organism suspension can be quantified at $2.28×10^8$ CFU/mL.

Results for the in situ Kirby-Bauer assay of PVC slides coated with a chlorhexidine containing coating that were not been subject to elution or were eluted for 14 days. Negative controls included a coated slide that did not contain chlorhexidine and a non-coated slide.

TABLE 1

| Sample | Time | Zone (mm) | | | | | | | | | | | | | | | | Avg Zone (mm) |
|---|---|---|---|---|---|---|---|---|---|---|---|---|---|---|---|---|---|---|
| Coated w/ Drug | Day 14 | 2 | 1 | 1 | 1 | 2 | 2 | 1 | 1 | 1 | 1 | 0.5 | 1 | 1 | 1 | 1 | 1 | 0.875 |
| Coated w/ Drug | Day 0 | 7 | 8 | 10 | 8 | 10 | 10 | 8 | 9 | 10 | 8 | 6 | 5 | 4 | 5 | 6 | 6 | 7.281 |
| Coated w/o Drug | | 0 | 0 | 0 | 0 | 0 | 0 | 0 | 0 | 0 | 0 | 0 | 0 | 0 | 0 | 0 | 0 | 0 |
| Non-Coated | | 0 | 0 | 0 | 0 | 0 | 0 | 0 | 0 | 0 | 0 | 0 | 0 | 0 | 0 | 0 | 0 | 0 |

Example 4

Microbial Anti-Adhesion to Superhydrophobic Surfaces

A superhydrophobic coating solution containing 10 g polycaprolactone (PCL, MW=80,000), 12 g LE3 particles, 400 mg Photocrosslinker A and 500 mL methyl acetate was applied to coupons (LDPE rod ¼ inch in diameter, McMaster-Carr, Chicago, Ill.) by dip coating. The coupons were lowered into the coating solution at 0.5 cm/sec, allowed to dwell in the coating solution for 30 seconds, and removed from the coating solution at 0.5 cm/sec. The coating solution was tightly capped when not in use and the bottle shaken to maintain proper suspension of the coating solution components. The coupons were air dried for 30 minutes under ambient conditions. Both the coated coupons and the uncoated coupons were subjected to ultraviolet light for 5 minutes (200-400 nm, Harland Medical UVM400, Eden Prairie, Minn.). The coupons were placed approximately 15 cm from the lamp (Harland Medical Systems, St. Paul, Minn.) and were rotating throughout the UV process. The UV process served to both crosslink the polymers in the coating as well as to sanitize the coupons.

A 1.8 mL suspension of *Staphylococcus aureus* ATCC#6538 (Microbiologics, St. Cloud, Minn.) (approximately $10^8$ CFU/mL which corresponds to a McFarland Nephelometer 2) was prepared in 1×PBS using a sterile swab, a small borosilicate test tube (12×75 mm), and a Vitek colorimeter.

In order to ensure that the coatings were neither over challenged nor under challenged, inoculum counts were performed. The original organism suspension (~$10^8$) was diluted 10-fold, 100-fold, and finally 100-fold into Butterfield's Buffer (PML brand, VWR). The resulting organism suspension density was approximately $10^3$. 100 µL of the $10^3$ suspension was spread plated to 100 mm Mueller-Hinton agar (resulting in a $10^2$ countable plate).

Within a biological safety cabinet, the coupons were dipped into the $10^3$ CFU/mL suspension (being careful not to dip above the coated portion of the coupon) for 15 seconds or 20 seconds. A stop watch was used to monitor the dwell time. After the coupons were removed from the organism suspension, they were placed in a milk dilution bottle containing 100 mL extraction buffer. The extraction buffer consisted of Butterfield's Buffer with 0.1% Tween added.

Additionally negative controls were performed. To ensure that this process was carried out under sterile conditions, a milk dilution bottle containing extraction buffer was subjected to the process with out a coupon. To assess the UV sanitization of the coupons an uncoated UV treated coupon was placed in milk dilution bottle containing extraction buffer (without dipping into the $10^3$ *S. aureus* suspension).

The milk dilution bottles were then placed on an orbital shaker for 30 minutes at approximately 200 rpm to release any bound organisms.

The extraction buffer was filtered through a Nalgene 0.45 µm filter (the coupon was left in the milk dilution bottle). 100 mL Butterfield's Buffer was added to the milk dilution bottle and the bottle placed on an orbital shaker for 5 minutes at approximately 200 rpm. The Butterfield's Buffer was filtered through the same 0.45 µm filter. The filter was removed from the filter unit via sterile forceps and placed on a 100 mm Mueller-Hinton agar plate. The plates were inverted and incubated at 37° C. for 18 hours. Upon removal from incubation, the number of colony forming units per plate or filter were counted. See Table 2 below.

Inoculum count plates: Plate 1=198 CFU/plate, Plate 2=211 CFU/plate. Average of Plate 1 & Plate 2: 204.5 CFU/plate.

Based on the inoculum count results, the $10^3$ organism dilution can be quantified at $2.05 \times 10^3$ CFU/mL.

Results for adhesion of *S. aureus* to coated and uncoated LDPE coupons when dipped in a $10^3$ CFU/mL of *S. aureus* for 20 seconds or 1 minute 15 seconds. Coupon 7 serves to assess the UV sanitization of the coupons. Coupon 8 serves to ensure that this process was carried out under sterile conditions.

TABLE 2

| Coupon # | Coated | $10^3$ S.a. Dip Time | Results | Avg: CFU/Filter | % CFU Reduction (CFU/coated coupon divided by CFU/ Uncoated coupon) |
|---|---|---|---|---|---|
| 1 | | 0:20 | 87 | 138 | |
| 2 | | 0:20 | 189 | | |
| 3 | ✓ | 0:20 | 0 | 0.5 | 99.64% |
| 4 | ✓ | 0:20 | 1 | | |
| 7 | | 0:00 | 0 | 0 | |
| 8 | | 0:00 | 0 | 0 | |

Example 5

Durability of Superhydrophobic Coating on PVC Slides

PVC slides (Rinzl brand, VWR, Batavia, Ill., 0.5 mm thick)) slides were cut into 0.5×3 inches and cleaned with isopropyl alcohol (IPA). The tare weights of each slide were recorded. The slides were spray coated with superhydrophobic coating solution. The superhydrophobic coating solution contained 10 g polycaprolactone (PCL, MW=80,000), 12 g LE3 particles, 400 mg Photocrosslinker A and 500 mL methyl acetate. The line pressure gauge on the nitrogen tank was set to 60 psi, while the pressure on the spray gun (Wagner Contractor Series, H VL P conversion gun, Wagner Spray Tech Corp. Mpls, Minn.) was set to 15 psi. The slides were placed on a holder and rotated 360° to get a uniform coating throughout the pieces. The coated slides were dried in 40° C. oven overnight. The weight was recorded after the drying process and illuminated under UV light for 5 minutes (200-400 nm, Harland Medical UVM400, Eden Prairie, Minn.). From the tare and gross weight measurements, the weight of the coating was determined (See Table 3).

TABLE 3

Recorded Tare, Gross and Net weights for each PVC slide.

| Sample | Bare slides mass (mg) | Slides and coating (mg) | Mass of coating (mg) |
|---|---|---|---|
| 3 | 673.6 | 717.9 | 44.3 |
| 5 | 662.3 | 707.6 | 45.3 |

Durability Testing

Two superhydrophobic coated PVC slides from the previous step were subjected to durability testing using a friction tester. The pieces were pulled 5 times at 100 g/cm$^2$ of force. The mass of the slides before and after the test were recorded. At the end of 5 pulls, the superhydrophobicity of the coating was examined by water stream application. (Table 4)

TABLE 4

| Sample | Initial mass of piece | After pull mass | Δ in mass (mg) | Mass of coating (mg) | % weight loss | SHPB |
|---|---|---|---|---|---|---|
| 3 | 717.9 | 717.3 | 0.6 | 44.3 | 1.4 | Y |
| 5 | 707.6 | 706.7 | 0.9 | 45.3 | 1.99 | Y |

Example 6

Superhydrophobic Coating Containing Drug Loaded Particles mPEG-PCL Polymer Synthesis Poly(ethylene glycol) methyl ether (3.5 g mPEG; Mn ca. 5000 g/mol; Aldrich Chemical Company Inc., Milwaukee Wis. 53233 USA) was transferred into a 50 mL round-bottom flask (24/40 joint) and dried under vacuum at 75° C. (oil bath) overnight prior to the polymerization. The dried mPEG starting material was maintained under vacuum at elevated temperature until ready for use. Epsilon-caprolactone (35 mL ε-CL; 99%; Sigma-Aldrich Inc., St. Louis Mo. 63173 USA) was freshly distilled immediately prior to use (115 millitorr; 63° C.).

The reaction flask containing mPEG was placed in an oil bath atop a magnetic stir plate and distilled ε-CL (15.5 mL, 0.141 mol) was poured into the reaction flask. A Teflon® stir bar was inserted into the reaction flask and began to stir. An inlet adapter with a hose fitting (24/40 joint) was attached to a flask and secured. The mixture was subjected to two cycles of vacuum drying (20 minutes) and argon purge (20 minutes) with a vacuum gas manifold prior to addition of tin (II) 2-ethylhexanoate (0.057 g, 0.14 mmol SnOct2; ~95%; Sigma-Aldrich Inc., St. Louis Mo. 63173 USA). After addition of the catalyst the reaction mixture was subjected to another cycle of vacuum drying and argon purge prior to being sealed with a glass stopper and secured by copper wire. The oil bath temperature was increased to 140-146° C. and the polymerization was allowed to proceed overnight while stirring. After cooling the polymer was dissolved in dichloromethane (200 mL) and precipitated into methanol (>2 L) while stirring with a mechanical stirrer. The polymer precipitate was allowed to settle after two hours collected. The collected material was vacuum dried overnight at 50° C. to yield a solid white product (12.34 g). $^1$H NMR analysis confirmed a Mn ca. 26000 g/mol.

Preparation of Chlorhexidine Encapsulated mPEG-PCL Particles

The synthesized polymer (1.270 g) from the previous example was dissolved in methyl acetate solvent with heating and vortexing in a 60 mL amber vial. Chlorhexidine (0.252 g; 98%; Sigma-Aldrich Inc., St. Louis Mo. 63173 USA) was massed out and added to the polymer solution. The solution was sonicated and vortexed to ensure that all the drug was dissolved. A 400 mL graduated beaker was filled with 150 mL of deionized water and placed under a mechanical stirrer located in a laboratory hood. The mechanical stirrer was set to 800 rpm and the polymer/drug solution was added dropwise over several hours forming a white suspension. Mechanical stirring was continued overnight until all the methyl acetate had evaporated. The aqueous particle suspension was filtered through a fritted disc filter under vacuum to eliminate large particle agglomerations and unencapsulated drug. The aqueous suspension was lyophilized to yield 0.930 g of white drug encapsulated polymer particles. The appearance of particles was confirmed with dilute aqueous solutions under a microscope. The loading level was determined to be 8.9% by UV analysis.

Superhydrophobic Coating Formulations Using PIB with Chlorhexidine Loaded Particles A stock solution of 20 mg/mL polyisobutylene, Mn ca. 2×10^6 (BASF, Ludwigshafen, Germany) was prepared in hexane. Fumed silica particles (Evonik Degussa GmbH, Essen, Germany) and two types of biodegradable chlorhexidine encapsulated particles were used to prepare coating formulations. The two types of biodegradable polymers used for these formulations were: (50:50) poly(DL lactide-co-glycolide) Mn ca. 40000-75000 g/mol (Sigma-Aldrich Inc., St. Louis Mo. 63173 USA) and the polymer mPEG-PCL. Chlorhexidine encapsulated particles with PLGA were prepared as described below for the chlorhexidine loaded mPEG-PCL particles. Table 5 below describes the coating formulations used to coat low density polyethylene (LDPE). The coating formulations were dip coated onto LDPE rods (4.5 cm long× 0.65 cm diameter) at a dip speed of 0.5 cm/sec. After drying, the coated samples were tested qualitatively for superhydrophobicity with deionized water and demonstrated the presence of a superhydrophobic surface by repelling the water droplets.

Preparation of Chlorhexidine Encapsulated PLGA Particles.

100 mg PLGA was dissolved by vortexing in 1 mL dichloromethane. To the polymer solution, 20 mg chlorhexidine was mixed and dispersed by probe sonication for 30 seconds. 4 mL 1% (w/v) aqueous PVA was added to the drug suspension and emulsified by homogenization for 30 seconds. The resultant oil-in-water (O/W) emulsion was poured into 30 mL of 0.3% (w/v) PVA solution and stirred for 45 minutes at room temperature. After the evaporation of the organic solvent, the hardened microparticles were collected by centrifugation at 1500 rpm for 10 minutes, washed three times with 5 mL deionized water, lypholized and stored under desiccation at −20° C.

TABLE 5

| Formulation | Stock solution | Silica particles | Biodegradable particles | Superhydrophobic (Y/N) |
|---|---|---|---|---|
| mPEG-PCL | 50 mL | 0.975 g | 0.260 g | Y |
| PLGA | 50 mL | 0.963 g | 0.264 g | Y |

Example 7

Superhydrophobic Coating Formulation Using PiBMA on Parylene Coated Discs

Parylene coated discs (8 mm dia.; V&P Scientific, Inc., San Diego, Calif. 92121 USA) were cleaned with isopropanol solvent and allowed to air dry before being spot deposit coated with 2×55 uL of coating formulation [30 mg/mL poly (isobutyl methacrylate) (Mw ca. 70000; PiBMA; Sigma-Aldrich Inc., St. Louis Mo. 63173 USA) and 15 mg/mL dexamethasone (Sigma-Aldrich Inc., St. Louis Mo. 63173 USA) in THF]. After allowing the disc coatings to dry the discs were spray coated with a superhydrophobic formulation (20 mg/mL PiBMA; 24 mg/mL fumed silica particles; 0.8 mg/mL photocrosslinker A in methyl acetate). The coated discs were vacuum oven dried at 30° C. overnight before being illuminated with UV lamp (2 min, 200-400 nm, Harland Medical UVM400, Eden Prairie, Minn.). The coated discs were tested using deionized water and found to be superhydrophobic by the repellence of the water droplets.

Example 8

Release of Dexamethasone from Superhydrophobic Surfaces

Preparation of Dexamethasone Solution

In a vial, 15 mg of dexamethasone (Sigma Aldrich Inc. St. Louis, Mo.) was dissolved in 1.5 mL of tetrahydrofuran (THF). To the solution, 30 mg polycaprolactone (PCL, MW=80 k) was added. The solution was shaken at room temperature overnight.

Coating Parylene Coated Stir Discs with Dexamethasone

Parylene coated stir discs (V&P Scientific Inc., San Diego, Calif.) (8.00 mm diameter, 0.685 mm thick) were cleaned with IPA. With a diamond tip pen, label the discs individually. The bare weights of the discs were recorded before the coating process. A 110 μL dexamethasone solution was dropped to the discs and dried at room temperature. The mass of each disc was recorded.

Coating Dexamethasone Discs with SHPB Coating

The dexamethasone discs were adhered to a cardboard using double stick tape. A premade SHPB solution with a composition of 10 g polycaprolactone (PCL, MW=80,000), 12 g LE3 particles and 400 mg Photocrosslinker A in 500 mL methyl acetate was used to coat the pieces. The solution was applied eight times with a spray gun to thoroughly coat the discs. The line pressure gauge on the nitrogen tank was set to 60 psi, while the pressure on the spray gun was set to 15 psi. The cardboard was horizontally rotated 180° to completely coat the discs. The discs were dried in a 30° C. vacuum oven overnight. After drying, the discs were weighed and illuminated under UV light for 2 minutes (200-400 nm, Harland Medical UVM400, Eden Praire, Minn.). Superhydrophobicity was tested on the coated discs by trying to place a ten microliter water droplet on the surface through manual micropipette; the droplets rolled on the surface indicating superhydrophobicity.

Coating Dexamethasone Discs with Non-Textured Top Coat

The dexamethasone discs were adhered to a cardboard using double stick tape A premade non-textured solution with a composition of 10 g polycaprolactone (PCL, MW=80,000), 12 g LE3 particles and 400 mg Photocrosslinker A and 500 mL methyl acetate was used to coat the pieces. The solution was applied eight times with a spray gun to thoroughly coat the discs. The line pressure gauge on the nitrogen tank was set to 60 psi, while the pressure on the spray gun was set to 15 psi. The cardboard was horizontally rotated 180° to completely coat the discs. The discs were dried in a 30° C. vacuum oven overnight. After drying, the discs were weighed and illuminated under UV light for 2 minutes (200-400 nm, Harland Medical UVM400, Eden Praire, Minn.). The non-textured top coat was not superhydrophobic as confirmed by being able to manually apply a ten microliter water droplet with a micropipette on the level surface without rolling of the drop.

Release Study

Figure 2:
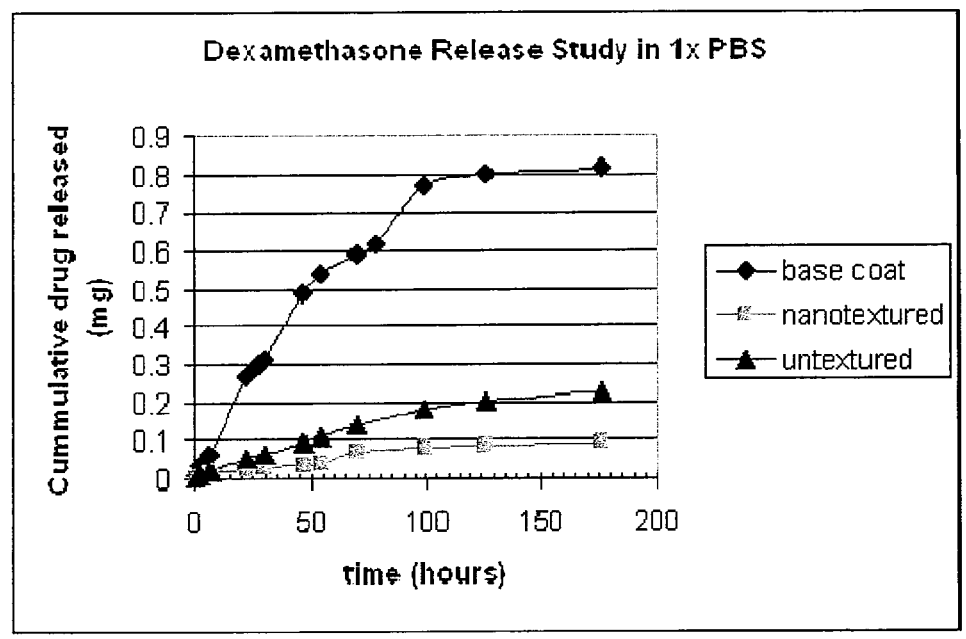
FIG. 2 depicts a dexamethasone release from a coating of the invention.

The discs, including basecoated dexamethasone, dexamethasone with superhydrophobic coating, and dexamethasone with a non-textured topcoat, were immersed individually in a conical tube containing 5 mL 1×PBS. The tubes were placed on a shaker in a 37° C. oven. At specific time points, the entire supernatant was removed and replaced with fresh 1× PBS. The concentration of the dexamethasone was determined and calculated by reading the absorbance of the supernatant at 240 and 278 nm. See FIG. 2.

Example 9

Release of Cyclosporin from a Superhydrophobic Surface

Preparation of Cyclosporin Solution

In a vial, 25 mg cyclosporin was dissolved in 2.5 mL of tetrahydrofuran (THF). To the solution, 50 mg polycaprolactone (PCL, MW=80k) was added. The solution was shaken at room temperature until PCL dissolved.

Coating Parylene Coated Stir Discs with Cyclosporin

Parylene coated stir discs (8.00 mm diameter, 0.685 mm thick) were cleaned with IPA. With a diamond tip pen, label the discs individually. The bare weights of the discs were recorded before the coating process. A 110 μL cyclosporin solution was dropped to the discs and dried at room temperature. The mass of each disc was recorded.

Coating Cyclosporin Discs with SHPB Coating

The cyclosporine discs were adhered to a cardboard using double stick tape. A premade SHPB solution with a composition of 10 g polycaprolactone (PCL, MW=80,000), 12 g LE3 particles and 400 mg Photocrosslinker A and 500 mL methyl acetate was used to coat the pieces. The solution was applied eight times with a spray gun to thoroughly coat the discs. The line pressure gauge on the nitrogen tank was set to 60 psi, while the pressure on the spray gun was set to 15 psi. The cardboard was horizontally rotated 180° to completely coat the discs. The discs were dried in a 30° C. vacuum oven overnight. After drying, the discs were weighed and illuminated under UV light for 2 minutes (200-400 mu, Harland Medical UVM400, Eden Praire, Minn.).

Release Study

Figure 3:
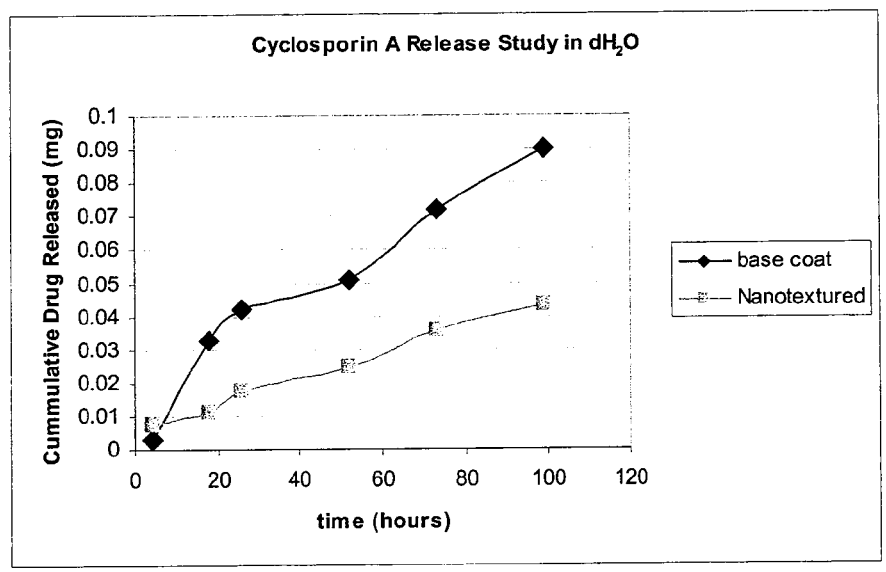
FIG. 3 depicts a cyclosporin release from a coating of the invention.

The discs, including basecoated cyclosporin and cyclosporin with superhydrophobic coating were immersed individually in a conical tube containing 5 mL deionized water. The tubes were placed on a shaker in a 37° C. oven. At specific time points, the entire supernatant was removed and replaced with fresh deionized water. The concentration of the cyclosporin was determined and calculated by reading the absorbance of the supernatant at 210 nm. See FIG. 3.

Example 10

Superhydrophobicity of a Drug-Containing Single-Layer Nanotextured Polymer Coat

PVC slides (Rinzl brand, VWR, Batavia, Ill., 0.5 mm thick) were cut into 55×12 mm sections, cleaned with IPA, and air dried. A coating solution of 5 mg/mL chlorhexidine (Sigma Aldrich, St. Louis, Mich.), 20 mg/mL poly-☐-caprolactone (PCL, ~80K g/mol, Aldrich Chemical Co. Milwaukee, Wis.), and 24 mg/mL LE3 particles (Evonik Industries, Essen, Germany), prepared in methyl acetate, was applied to the slides by a dipcoat method. The slides were dipped into the basecoat solution and after a 30 sec dwell, the slides were withdrawn at a rate 5 cm/sec. The coated slides were cured by solvent evaporation at room temperature, resulting in a chlorhexidine-containing nanotextured polymer surface coating. The superhydrophobicity of the nanotextured surface coating was confirmed. A ten microliter water droplet applied manually by a micropipette could not be placed on the level surface without rolling and a stream of water was repelled by the surface as shown by water droplets bouncing off of the surface.

Example 11

Balloon Inflation of Superhydrophobic Coating on an Endotracheal Tube

An endotracheal tube (Cuffed, Murphy 7.0 mm, Hi-Lo®, Tyco Healthcare group, Nellcor Puritan Bennet Division, Pleasant Calif.) was coated using a spray gun with the coating described in the topcoat of Example 2. After air drying for 30 minutes, the coating was cured for 5 minutes using the UVM 400 lamp. A syringe was used to inflate and deflate the balloon on the endotracheal tube for four cycles. The balloon was then inspected microscopically (50×) for cracking and tested for superhydrophobicity as described. No cracking could be observed and superhydrophobicity was maintained after balloon inflation.

Example 12

Superhydrophobic Coatings with a Crosslinker and Initiator

A coating formulation of 0.02 mg/ml Photocrosslinker A, 0.54 mg/ml benzophenone (Aldrich, Milwaukee, Wis.), 5 mg/ml polybutylmethacrylate (Aldrich, Milwaukee, Wis.), and 6 mg/ml fumed silica (LE3 Aerosil, Evonik Industries, Essen, Germany) was prepared. This formulation was spray coated on nylon fabric then illuminated with the UVM light for 5 minutes. The resulting coating was tested for superhydrophobicity as described.

Example 13

Superhydrophobic Drug Eluting Coatings with a Crosslinker and an Initiator

A drug-containing base layer such as those described in any of Examples 2 (chlorhexidine), 8 (dexamethasone) or 9 (cyclosporin) is prepared and coated on parylene discs. The superhydrophobic coating as described in Example 12 could be is used as a topcoat by spray application of the formulation, followed by UV illumination with the UVM 400 lamp. The resulting coating shows superhydrophobic properties and elutes drug in a controlled manner.

Example 14

Superhydrophobic Drug Eluting Coatings with Alternate Crosslinkers

A drug-containing base layer such as those described in any of Examples 2 (chlorhexidine), 8 (dexamethasone) or 9 (cyclosporin) is prepared and coated on parylene discs. The superhydrophobic coating as described in Example 13 of U.S. patent application Ser. No. 11/457,170 is applied as a topcoat by spray application of the formulation, followed by UV illumination the UVM 400 lamp. The resulting coating shows superhydrophobic properties and elutes drug in a controlled manner.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A superhydrophobic coating comprising:
a first hydrophobic binder;
a plurality of particles comprising a size between about 1 nm to about 25 microns;
a bioactive agent, and
a crosslinker, wherein the crosslinker has a formula:

wherein L is a linking group, comprising the formula according to structure (I):

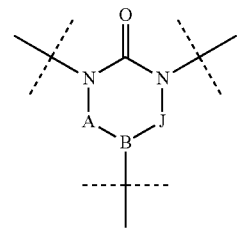

wherein A and J are each independently a hydrogen atom, an alkyl group, an aryl group, or together with B form a cyclic ring, provided when A and J are each independently a hydrogen atom, an alkyl group, or an aryl group then B is not present;
B is $NR^{11}$, O, or $(-CH_2-)_z$;
provided when A, B and J form a ring, then A and J are $(-CH_2-)_z$, or $C=O$;
$R^{11}$ is a hydrogen atom, an alkyl group, an aryl group or denotes a bond with T
each z independently is an integer from 0 to 3; and
provided when either A or J is $C=O$, then B is $NR^{11}$, O, or $(-CH_2-)_z$ and z must be at least 1;

T is (—CH$_2$—)$_x$,(—CH$_2$CH$_2$—O—)$_x$,(—CH$_2$CH$_2$CH$_2$—O—)$_x$,(—CH$_2$CH$_2$CH$_2$CH$_2$—O—)$_x$ or forms a bond;

R$^1$ is a hydrogen atom, an alkyl, alkyloxyalkyl, aryl, aryloxyalkyl or aryloxyaryl group;

X is O, S, or NR$^8$R$^9$;

P is a hydrogen atom or a protecting group, with the proviso that P is absent when X is NR$^8$R$^9$;

R$^2$ is a hydrogen atom, an alkyl, alkyloxyalkyl, aryl, aryloxyalkyl or aryloxyaryl group;

G is O, S, SO, SO$_2$, NR$^{10}$,(CH$_2$)$_r$—O— or C═O;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C═O(—CH$_2$—)$_s$,(—CH$_2$—)$_r$S(—CH$_2$—)$_s$, (—CH$_2$—)$_r$S═O(—CH$_2$—)$_s$ or (—CH$_2$—)$_r$S(O)$_2$(—CH$_2$—)$_s$,(—CH$_2$—)$_r$NR(—CH$_2$—)$_s$;

R$^{10}$ is a hydrogen atom or an alkyl, aryl or arylalkyl group;

R$^8$ and R$^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10; and x is an integer from 1 to about 500.

2. The coating of claim 1, wherein the particles are dispersed throughout the bulk of the coating.

3. The coating of claim 1, wherein the particles are present in a weight ratio of particles to polymeric binder of 1:1 to 4:1.

4. The coating of claim 1, further comprising an initiator.

5. The coating of claim 1, wherein the hydrophobic polymeric binder has a surface tension of less than about 50 mN/m.

6. The coating of claim 1, wherein the hydrophobic binder is a hydrophobic polymer that is a homopolymer or copolymer of a polyalkylene, a polyacrylate, a polymethacrylate, a polyester, a polyamide, a polyurethane, a polyvinylarylene, a polyvinyl ester, a polyvinylarylene/alkylene copolymer, a polyalkyleneoxide, a polyvinyl halide, or mixtures thereof.

7. The coating of claim 4, wherein the crosslinker has more than one acrylate, methacrylate, vinyl or arylketone containing moiety.

8. The coating of claim 4, wherein the initiator, when present, is benzophenone, an acetophenone derivative, a peroxide, a peroxy compound, a benzoin derivative, a benzilketal, a hydroxyalkylphenone, an aminoalkylphenone, an O-acyl oximoketone, an acylphosphine oxides, an acylphosphonate, a thiobenzoic S-ester, an azo or azide compound, a triazine, a 1,2 diketone, a quinone, a coumarins, a xanthone, azobis-isobutyronitrile or a mixture thereof.

9. The coating of claim 1, wherein the particles are aluminum oxides, titanium oxide, zirconium oxide, organothiolated gold, organothiolated silver, silanated silver, nickel, nickel oxide, iron oxide, polystyrene particles, (meth)acrylates particles, polytetrafluroethylene particles, silica particles, polyolefin particles, polycarbonate particles, polysiloxane particles, silicone particles, polyester particles, polyamide particles, polyurethane particles, ethylenically unsaturated polymer particles, polyanhydride particles, polycaprolactone (PCL), polylactideglycolide (PLGA), nanofibers, nanotubes, or nanowires, or combinations thereof.

10. The coating of claim 1, wherein the bioactive agent is an anti-inflammatory, an antimicrobial or an antibiotic.

11. A composite comprising:

a substrate; and the coating of claim 1 coated onto the substrate.

* * * * *